US012661488B2

(12) United States Patent
Kiani et al.

(10) Patent No.: US 12,661,488 B2
(45) Date of Patent: Jun. 23, 2026

(54) MODULAR WEARABLE DEVICE FOR PATIENT MONITORING AND DRUG ADMINISTRATION

(71) Applicant: Willow Laboratories, Inc., Irvine, CA (US)

(72) Inventors: Massi Joe E. Kiani, Laguna Niguel, CA (US); Kevin Hughes Pauley, Lake Forest, CA (US); Hung The Vo, Fountain Valley, CA (US); Gerry Hammarth, Irvine, CA (US); Gregory A. Olsen, Lake Forest, CA (US)

(73) Assignee: Willow Laboratories, Inc., Irvine, CA (US)

( * ) Notice: Subject to any disclaimer, the term of this patent is extended or adjusted under 35 U.S.C. 154(b) by 633 days.

(21) Appl. No.: 18/155,978

(22) Filed: Jan. 18, 2023

(65) Prior Publication Data

US 2023/0226331 A1    Jul. 20, 2023

Related U.S. Application Data

(60) Provisional application No. 63/300,426, filed on Jan. 18, 2022.

(51) Int. Cl.
| | |
|---|---|
| *A61M 31/00* | (2006.01) |
| *A61B 5/00* | (2006.01) |
| *A61M 5/142* | (2006.01) |
| *A61M 5/172* | (2006.01) |

(52) U.S. Cl.
CPC ......... *A61M 31/002* (2013.01); *A61B 5/6823* (2013.01); *A61B 5/6824* (2013.01); *A61B 5/6828* (2013.01); *A61B 5/7271* (2013.01)

(58) Field of Classification Search
CPC .......... A61M 31/002; A61M 2230/201; A61M 2230/435; A61M 5/14244; A61M 2005/14268; A61M 2005/1726; A61M 2230/432; A61M 5/1723; A61M 2005/3022; A61M 2209/088; A61B 5/6823; A61B 5/6824; A61B 5/6828; A61B 5/7271; A61B 2560/0443; A61B 5/14532; A61B 5/4839
See application file for complete search history.

(56) References Cited

U.S. PATENT DOCUMENTS

| | | | |
|---|---|---|---|
| 4,919,596 A | 4/1990 | Slate et al. | |
| 4,960,128 A | 10/1990 | Gordon et al. | |
| 4,964,408 A | 10/1990 | Hink et al. | |
| 5,319,355 A | 6/1994 | Russek | |

(Continued)

OTHER PUBLICATIONS

US 2024/0016391 A1, 01/2024, Lapotko et al. (withdrawn)

(Continued)

*Primary Examiner* — Jason E Flick
(74) *Attorney, Agent, or Firm* — KNOBBE, MARTENS, OLSON & BEAR, LLP

(57) ABSTRACT

A modular, wearable sensor and drug administration device is disclosed. The device includes removable modules such as sensors and drug administration apparatuses within a single wearable device. The device may be comfortable and modules may be easily removed and replaced. The sensors and drug administration devices may be used in concert to monitor and administer drug to a patient. Such a device may improve a patient's quality of life.

17 Claims, 11 Drawing Sheets

(56)　　　　　References Cited

U.S. PATENT DOCUMENTS

| | | | |
|---|---|---|---|
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |
| 5,431,170 | A | 7/1995 | Mathews |
| 5,436,499 | A | 7/1995 | Namavar et al. |
| D361,840 | S | 8/1995 | Savage et al. |
| D362,063 | S | 9/1995 | Savage et al. |
| D363,120 | S | 10/1995 | Savage et al. |
| 5,456,252 | A | 10/1995 | Vari et al. |
| 5,479,934 | A | 1/1996 | Imran |
| 5,482,036 | A | 1/1996 | Diab et al. |
| 5,494,043 | A | 2/1996 | O'Sullivan et al. |
| 5,533,511 | A | 7/1996 | Kaspari et al. |
| 5,561,275 | A | 10/1996 | Savage et al. |
| 5,590,649 | A | 1/1997 | Caro et al. |
| 5,602,924 | A | 2/1997 | Durand et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,671,914 | A | 9/1997 | Kalkhoran et al. |
| 5,726,440 | A | 3/1998 | Kalkhoran et al. |
| D393,830 | S | 4/1998 | Tobler et al. |
| 5,743,262 | A | 4/1998 | Lepper, Jr. et al. |
| 5,747,806 | A | 5/1998 | Khalil et al. |
| 5,750,994 | A | 5/1998 | Schlager |
| 5,758,644 | A | 6/1998 | Diab et al. |
| 5,760,910 | A | 6/1998 | Lepper, Jr. et al. |
| 5,890,929 | A | 4/1999 | Mills et al. |
| 5,919,134 | A | 7/1999 | Diab |
| 5,987,343 | A | 11/1999 | Kinast |
| 5,997,343 | A | 12/1999 | Mills et al. |
| 6,002,952 | A | 12/1999 | Diab et al. |
| 6,010,937 | A | 1/2000 | Karam et al. |
| 6,027,452 | A | 2/2000 | Flaherty et al. |
| 6,040,578 | A | 3/2000 | Malin et al. |
| 6,066,204 | A | 5/2000 | Haven |
| 6,083,248 | A | 7/2000 | Thompson |
| 6,115,673 | A | 9/2000 | Malin et al. |
| 6,124,597 | A | 9/2000 | Shehada et al. |
| 6,128,521 | A | 10/2000 | Marro et al. |
| 6,129,675 | A | 10/2000 | Jay |
| 6,144,868 | A | 11/2000 | Parker |
| 6,152,754 | A | 11/2000 | Gerhardt et al. |
| 6,184,521 | B1 | 2/2001 | Coffin, IV et al. |
| 6,232,609 | B1 | 5/2001 | Snyder et al. |
| 6,241,683 | B1 | 6/2001 | Macklem et al. |
| 6,253,097 | B1 | 6/2001 | Aronow et al. |
| 6,255,708 | B1 | 7/2001 | Sudharsanan et al. |
| 6,280,381 | B1 | 8/2001 | Malin et al. |
| 6,285,896 | B1 | 9/2001 | Tobler et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,334,065 | B1 | 12/2001 | Al-Ali et al. |
| 6,360,114 | B1 | 3/2002 | Diab et al. |
| 6,368,283 | B1 | 4/2002 | Xu et al. |
| 6,411,373 | B1 | 6/2002 | Garside et al. |
| 6,415,167 | B1 | 7/2002 | Blank et al. |
| 6,423,035 | B1 | 7/2002 | Das et al. |
| 6,427,088 | B1 | 7/2002 | Bowman et al. |
| 6,430,437 | B1 | 8/2002 | Marro |
| 6,430,525 | B1 | 8/2002 | Weber et al. |
| 6,463,311 | B1 | 10/2002 | Diab |
| 6,470,199 | B1 | 10/2002 | Kopotic et al. |
| 6,487,429 | B2 | 11/2002 | Hockersmith et al. |
| 6,505,059 | B1 | 1/2003 | Kollias et al. |
| 6,525,386 | B1 | 2/2003 | Mills et al. |
| 6,526,300 | B1 | 2/2003 | Kiani et al. |
| 6,534,012 | B1 | 3/2003 | Hazen et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,587,196 | B1 | 7/2003 | Stippick et al. |
| 6,587,199 | B1 | 7/2003 | Luu |
| 6,595,316 | B2 | 7/2003 | Cybulski et al. |
| 6,597,932 | B2 | 7/2003 | Tian et al. |
| 6,606,511 | B1 | 8/2003 | Ali et al. |
| 6,635,559 | B2 | 10/2003 | Greenwald et al. |
| 6,639,668 | B1 | 10/2003 | Trepagnier |
| 6,640,116 | B2 | 10/2003 | Diab |
| 6,640,117 | B2 | 10/2003 | Makarewicz et al. |
| 6,658,276 | B2 | 12/2003 | Kiani et al. |
| 6,661,161 | B1 | 12/2003 | Lanzo et al. |
| 6,697,656 | B1 | 2/2004 | Al-Ali |
| 6,697,658 | B2 | 2/2004 | Al-Ali |
| RE38,476 | E | 3/2004 | Diab et al. |
| RE38,492 | E | 4/2004 | Diab et al. |
| 6,738,652 | B2 | 5/2004 | Mattu et al. |
| 6,760,607 | B2 | 7/2004 | Al-Ali |
| 6,788,965 | B2 | 9/2004 | Ruchti et al. |
| 6,816,241 | B2 | 11/2004 | Grubisic |
| 6,822,564 | B2 | 11/2004 | Al-Ali |
| 6,850,787 | B2 | 2/2005 | Weber et al. |
| 6,850,788 | B2 | 2/2005 | Al-Ali |
| 6,876,931 | B2 | 4/2005 | Lorenz et al. |
| 6,916,159 | B2 | 7/2005 | Rush et al. |
| 6,920,345 | B2 | 7/2005 | Al-Ali et al. |
| 6,934,570 | B2 | 8/2005 | Kiani et al. |
| 6,943,348 | B1 | 9/2005 | Coffin, IV |
| 6,956,649 | B2 | 10/2005 | Acosta et al. |
| 6,961,598 | B2 | 11/2005 | Diab |
| 6,970,792 | B1 | 11/2005 | Diab |
| 6,985,764 | B2 | 1/2006 | Mason et al. |
| 6,990,364 | B2 | 1/2006 | Ruchti et al. |
| 6,998,247 | B2 | 2/2006 | Monfre et al. |
| 7,003,338 | B2 | 2/2006 | Weber et al. |
| 7,015,451 | B2 | 3/2006 | Dalke et al. |
| 7,027,849 | B2 | 4/2006 | Al-Ali |
| D526,719 | S | 8/2006 | Richie, Jr. et al. |
| 7,096,052 | B2 | 8/2006 | Mason et al. |
| 7,096,054 | B2 | 8/2006 | Abdul-Hafiz et al. |
| D529,616 | S | 10/2006 | Deros et al. |
| 7,133,710 | B2 | 11/2006 | Acosta et al. |
| 7,142,901 | B2 | 11/2006 | Kiani et al. |
| 7,225,006 | B2 | 5/2007 | Al-Ali et al. |
| RE39,672 | E | 6/2007 | Shehada et al. |
| 7,254,429 | B2 | 8/2007 | Schurman et al. |
| 7,254,431 | B2 | 8/2007 | Al-Ali et al. |
| 7,254,434 | B2 | 8/2007 | Schulz et al. |
| 7,274,955 | B2 | 9/2007 | Kiani et al. |
| D554,263 | S | 10/2007 | Al-Ali et al. |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,356,365 | B2 | 4/2008 | Schurman |
| 7,371,981 | B2 | 5/2008 | Abdul-Hafiz |
| 7,373,193 | B2 | 5/2008 | Al-Ali et al. |
| 7,377,794 | B2 | 5/2008 | Al-Ali et al. |
| 7,395,158 | B2 | 7/2008 | Monfre et al. |
| 7,415,297 | B2 | 8/2008 | Al-Ali et al. |
| 7,438,683 | B2 | 10/2008 | Al-Ali et al. |
| 7,483,729 | B2 | 1/2009 | Al-Ali et al. |
| D587,657 | S | 3/2009 | Al-Ali et al. |
| 7,500,950 | B2 | 3/2009 | Al-Ali et al. |
| 7,509,494 | B2 | 3/2009 | Al-Ali |
| 7,510,849 | B2 | 3/2009 | Schurman et al. |
| 7,514,725 | B2 | 4/2009 | Wojtczuk et al. |
| 7,519,406 | B2 | 4/2009 | Blank et al. |
| D592,507 | S | 5/2009 | Wachman et al. |
| 7,530,942 | B1 | 5/2009 | Diab |
| 7,547,281 | B2 | 6/2009 | Hayes et al. |
| 7,593,230 | B2 | 9/2009 | Abul-Haj et al. |
| 7,596,398 | B2 | 9/2009 | Al-Ali et al. |
| 7,606,608 | B2 | 10/2009 | Blank et al. |
| 7,620,674 | B2 | 11/2009 | Ruchti et al. |
| D606,659 | S | 12/2009 | Kiani et al. |
| 7,629,039 | B2 | 12/2009 | Eckerbom et al. |
| 7,640,140 | B2 | 12/2009 | Ruchti et al. |

(56) References Cited

U.S. PATENT DOCUMENTS

| | | | |
|---|---|---|---|
| 7,647,083 | B2 | 1/2010 | Al-Ali et al. |
| D609,193 | S | 2/2010 | Al-Ali et al. |
| D614,305 | S | 4/2010 | Al-Ali et al. |
| 7,697,966 | B2 | 4/2010 | Monfre et al. |
| 7,698,105 | B2 | 4/2010 | Ruchti et al. |
| RE41,317 | E | 5/2010 | Parker |
| RE41,333 | E | 5/2010 | Blank et al. |
| 7,729,733 | B2 | 6/2010 | Al-Ali et al. |
| 7,761,127 | B2 | 7/2010 | Al-Ali et al. |
| 7,764,982 | B2 | 7/2010 | Dalke et al. |
| D621,516 | S | 8/2010 | Kiani et al. |
| 7,791,155 | B2 | 9/2010 | Diab |
| RE41,912 | E | 11/2010 | Parker |
| 7,880,626 | B2 | 2/2011 | Al-Ali et al. |
| 7,909,772 | B2 | 3/2011 | Popov et al. |
| 7,919,713 | B2 | 4/2011 | Al-Ali et al. |
| 7,937,128 | B2 | 5/2011 | Al-Ali |
| 7,937,129 | B2 | 5/2011 | Mason et al. |
| 7,941,199 | B2 | 5/2011 | Kiani |
| 7,957,780 | B2 | 6/2011 | Lamego et al. |
| 7,962,188 | B2 | 6/2011 | Kiani et al. |
| 7,976,472 | B2 | 7/2011 | Kiani |
| 7,990,382 | B2 | 8/2011 | Kiani |
| 7,999,674 | B2 | 8/2011 | Kamen |
| 8,008,088 | B2 | 8/2011 | Bellott et al. |
| RE42,753 | E | 9/2011 | Kiani-Azarbayjany et al. |
| 8,028,701 | B2 | 10/2011 | Al-Ali et al. |
| 8,048,040 | B2 | 11/2011 | Kiani |
| 8,050,728 | B2 | 11/2011 | Al-Ali et al. |
| RE43,169 | E | 2/2012 | Parker |
| 8,118,620 | B2 | 2/2012 | Al-Ali et al. |
| 8,118,782 | B2 | 2/2012 | Remde |
| 8,130,105 | B2 | 3/2012 | Al-Ali et al. |
| 8,182,443 | B1 | 5/2012 | Kiani |
| 8,190,223 | B2 | 5/2012 | Al-Ali et al. |
| 8,192,394 | B2 | 6/2012 | Estes et al. |
| 8,203,438 | B2 | 6/2012 | Kiani et al. |
| 8,203,704 | B2 | 6/2012 | Merritt et al. |
| 8,219,172 | B2 | 7/2012 | Schurman et al. |
| 8,224,411 | B2 | 7/2012 | Al-Ali et al. |
| 8,229,532 | B2 | 7/2012 | Davis |
| 8,233,955 | B2 | 7/2012 | Al-Ali et al. |
| 8,255,026 | B1 | 8/2012 | Al-Ali |
| 8,265,723 | B1 | 9/2012 | McHale et al. |
| 8,274,360 | B2 | 9/2012 | Sampath et al. |
| 8,280,473 | B2 | 10/2012 | Al-Ali |
| 8,294,581 | B2 | 10/2012 | Kamen |
| 8,315,683 | B2 | 11/2012 | Al-Ali et al. |
| RE43,860 | E | 12/2012 | Parker |
| 8,346,330 | B2 | 1/2013 | Lamego |
| 8,353,842 | B2 | 1/2013 | Al-Ali et al. |
| 8,355,766 | B2 | 1/2013 | MacNeish, III et al. |
| 8,374,665 | B2 | 2/2013 | Lamego |
| 8,388,353 | B2 | 3/2013 | Kiani et al. |
| 8,401,602 | B2 | 3/2013 | Kiani |
| 8,414,499 | B2 | 4/2013 | Al-Ali et al. |
| 8,414,563 | B2 | 4/2013 | Kamen et al. |
| 8,418,524 | B2 | 4/2013 | Al-Ali |
| 8,428,967 | B2 | 4/2013 | Olsen et al. |
| 8,430,817 | B1 | 4/2013 | Al-Ali et al. |
| 8,437,825 | B2 | 5/2013 | Dalvi et al. |
| 8,455,290 | B2 | 6/2013 | Siskavich |
| 8,457,707 | B2 | 6/2013 | Kiani |
| 8,471,713 | B2 | 6/2013 | Poeze et al. |
| 8,473,020 | B2 | 6/2013 | Kiani et al. |
| 8,509,867 | B2 | 8/2013 | Workman et al. |
| 8,515,509 | B2 | 8/2013 | Bruinsma et al. |
| 8,523,781 | B2 | 9/2013 | Al-Ali |
| 8,527,298 | B2 | 9/2013 | Darling et al. |
| D692,145 | S | 10/2013 | Al-Ali et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| 8,577,431 | B2 | 11/2013 | Lamego et al. |
| 8,584,345 | B2 | 11/2013 | Al-Ali et al. |
| 8,585,377 | B2 | 11/2013 | Kamen |
| 8,588,880 | B2 | 11/2013 | Abdul-Hafiz et al. |
| 8,597,274 | B2 | 12/2013 | Sloan et al. |
| 8,613,724 | B2 | 12/2013 | Lanier et al. |
| 8,630,691 | B2 | 1/2014 | Lamego et al. |
| 8,641,631 | B2 | 2/2014 | Sierra et al. |
| 8,652,060 | B2 | 2/2014 | Al-Ali |
| 8,666,468 | B1 | 3/2014 | Al-Ali |
| 8,670,811 | B2 | 3/2014 | O'Reilly |
| 8,679,060 | B2 | 3/2014 | Mernoe et al. |
| RE44,823 | E | 4/2014 | Parker |
| RE44,875 | E | 4/2014 | Kiani et al. |
| 8,688,183 | B2 | 4/2014 | Bruinsma et al. |
| 8,690,799 | B2 | 4/2014 | Telfort et al. |
| 8,702,627 | B2 | 4/2014 | Telfort et al. |
| 8,712,494 | B1 | 4/2014 | MacNeish, III et al. |
| 8,715,206 | B2 | 5/2014 | Telfort et al. |
| 8,723,677 | B1 | 5/2014 | Kiani |
| 8,740,792 | B1 | 6/2014 | Kiani et al. |
| 8,755,535 | B2 | 6/2014 | Telfort et al. |
| 8,755,872 | B1 | 6/2014 | Marinow |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,781,544 | B2 | 7/2014 | Al-Ali et al. |
| 8,784,364 | B2 | 7/2014 | Kamen et al. |
| 8,790,268 | B2 | 7/2014 | Al-Ali |
| 8,801,613 | B2 | 8/2014 | Al-Ali et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,840,549 | B2 | 9/2014 | Al-Ali et al. |
| 8,852,094 | B2 | 10/2014 | Al-Ali et al. |
| 8,852,994 | B2 | 10/2014 | Wojtczuk et al. |
| 8,897,847 | B2 | 11/2014 | Al-Ali |
| 8,911,377 | B2 | 12/2014 | Al-Ali |
| 8,989,831 | B2 | 3/2015 | Al-Ali et al. |
| 8,998,809 | B2 | 4/2015 | Kiani |
| 9,066,666 | B2 | 6/2015 | Kiani |
| 9,066,680 | B1 | 6/2015 | Al-Ali et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,131,881 | B2 | 9/2015 | Diab et al. |
| 9,132,227 | B2 | 9/2015 | Bryant et al. |
| 9,138,180 | B1 | 9/2015 | Coverston et al. |
| 9,153,112 | B1 | 10/2015 | Kiani et al. |
| 9,180,245 | B2 | 11/2015 | Bryant et al. |
| 9,192,329 | B2 | 11/2015 | Al-Ali |
| 9,192,351 | B1 | 11/2015 | Telfort et al. |
| 9,195,385 | B2 | 11/2015 | Al-Ali et al. |
| 9,205,188 | B2 | 12/2015 | Lanigan et al. |
| 9,211,095 | B1 | 12/2015 | Al-Ali |
| 9,218,454 | B2 | 12/2015 | Kiani et al. |
| 9,245,668 | B1 | 1/2016 | Vo et al. |
| 9,267,572 | B2 | 2/2016 | Barker et al. |
| 9,277,880 | B2 | 3/2016 | Poeze et al. |
| 9,307,928 | B1 | 4/2016 | Al-Ali et al. |
| 9,323,894 | B2 | 4/2016 | Kiani |
| D755,392 | S | 5/2016 | Hwang et al. |
| 9,326,712 | B1 | 5/2016 | Kiani |
| 9,392,945 | B2 | 7/2016 | Al-Ali et al. |
| 9,408,542 | B1 | 8/2016 | Kinast et al. |
| 9,436,645 | B2 | 9/2016 | Al-Ali et al. |
| 9,445,759 | B1 | 9/2016 | Lamego et al. |
| 9,474,474 | B2 | 10/2016 | Lamego et al. |
| 9,480,435 | B2 | 11/2016 | Olsen |
| 9,510,779 | B2 | 12/2016 | Poeze et al. |
| 9,517,024 | B2 | 12/2016 | Kiani et al. |
| 9,532,722 | B2 | 1/2017 | Lamego et al. |
| 9,560,996 | B2 | 2/2017 | Kiani |
| 9,579,039 | B2 | 2/2017 | Jansen et al. |
| 9,604,001 | B2 | 3/2017 | Kamen |
| 9,622,692 | B2 | 4/2017 | Lamego et al. |
| D788,312 | S | 5/2017 | Al-Ali et al. |
| 9,649,054 | B2 | 5/2017 | Lamego et al. |
| 9,669,161 | B2 | 6/2017 | Bryant et al. |
| 9,687,602 | B2 | 6/2017 | Murphy et al. |
| 9,697,928 | B2 | 7/2017 | Al-Ali et al. |

(56) References Cited

U.S. PATENT DOCUMENTS

| | | | |
|---|---|---|---|
| 9,717,458 | B2 | 8/2017 | Lamego et al. |
| 9,724,016 | B1 | 8/2017 | Al-Ali et al. |
| 9,724,024 | B2 | 8/2017 | Al-Ali |
| 9,724,025 | B1 | 8/2017 | Kiani et al. |
| 9,737,656 | B2 | 8/2017 | Rosinko |
| 9,749,232 | B2 | 8/2017 | Sampath et al. |
| 9,750,442 | B2 | 9/2017 | Olsen |
| 9,750,461 | B1 | 9/2017 | Telfort |
| 9,750,896 | B2 | 9/2017 | Kamen et al. |
| 9,775,545 | B2 | 10/2017 | Al-Ali et al. |
| 9,778,079 | B1 | 10/2017 | Al-Ali et al. |
| 9,782,077 | B2 | 10/2017 | Lamego et al. |
| 9,787,568 | B2 | 10/2017 | Lamego et al. |
| 9,808,188 | B1 | 11/2017 | Perea et al. |
| 9,839,379 | B2 | 12/2017 | Al-Ali et al. |
| 9,839,381 | B1 | 12/2017 | Weber et al. |
| 9,847,749 | B2 | 12/2017 | Kiani et al. |
| 9,848,800 | B1 | 12/2017 | Lee et al. |
| 9,861,298 | B2 | 1/2018 | Eckerbom et al. |
| 9,861,305 | B1 | 1/2018 | Weber et al. |
| 9,877,650 | B2 | 1/2018 | Muhsin et al. |
| 9,891,079 | B2 | 2/2018 | Dalvi |
| 9,924,897 | B1 | 3/2018 | Abdul-Hafiz |
| 9,931,461 | B2 | 4/2018 | Kamen et al. |
| 9,936,917 | B2 | 4/2018 | Poeze et al. |
| 9,955,937 | B2 | 5/2018 | Telfort |
| 9,965,946 | B2 | 5/2018 | Al-Ali et al. |
| 9,968,730 | B2 | 5/2018 | Blumberg et al. |
| D820,865 | S | 6/2018 | Muhsin et al. |
| 9,986,952 | B2 | 6/2018 | Dalvi et al. |
| D822,215 | S | 7/2018 | Al-Ali et al. |
| D822,216 | S | 7/2018 | Barker et al. |
| 10,010,276 | B2 | 7/2018 | Al-Ali et al. |
| 10,086,138 | B1 | 10/2018 | Novak, Jr. |
| 10,105,286 | B2 | 10/2018 | Lanier et al. |
| 10,111,591 | B2 | 10/2018 | Dyell et al. |
| D833,624 | S | 11/2018 | DeJong et al. |
| 10,123,729 | B2 | 11/2018 | Dyell et al. |
| D835,282 | S | 12/2018 | Barker et al. |
| D835,283 | S | 12/2018 | Barker et al. |
| D835,284 | S | 12/2018 | Barker et al. |
| D835,285 | S | 12/2018 | Barker et al. |
| 10,149,616 | B2 | 12/2018 | Al-Ali et al. |
| 10,154,815 | B2 | 12/2018 | Al-Ali et al. |
| 10,159,412 | B2 | 12/2018 | Lamego et al. |
| 10,188,348 | B2 | 1/2019 | Al-Ali et al. |
| RE47,218 | E | 2/2019 | Al-Ali |
| RE47,244 | E | 2/2019 | Kiani et al. |
| RE47,249 | E | 2/2019 | Kiani et al. |
| 10,195,343 | B2 | 2/2019 | Kamen et al. |
| 10,205,291 | B2 | 2/2019 | Scruggs et al. |
| 10,226,187 | B2 | 3/2019 | Al-Ali et al. |
| 10,231,657 | B2 | 3/2019 | Al-Ali et al. |
| 10,231,670 | B2 | 3/2019 | Blank et al. |
| 10,232,113 | B2 | 3/2019 | Palerm |
| 10,238,794 | B2 | 3/2019 | Kamen et al. |
| 10,242,159 | B2 | 3/2019 | Kamen et al. |
| RE47,353 | E | 4/2019 | Kiani et al. |
| 10,279,247 | B2 | 5/2019 | Kiani |
| 10,292,664 | B2 | 5/2019 | Al-Ali |
| 10,299,720 | B2 | 5/2019 | Brown et al. |
| 10,327,337 | B2 | 6/2019 | Schmidt et al. |
| 10,327,713 | B2 | 6/2019 | Barker et al. |
| 10,332,630 | B2 | 6/2019 | Al-Ali |
| 10,363,342 | B2 | 7/2019 | Dillon et al. |
| 10,383,520 | B2 | 8/2019 | Wojtczuk et al. |
| 10,383,527 | B2 | 8/2019 | Al-Ali |
| 10,388,120 | B2 | 8/2019 | Muhsin et al. |
| D864,120 | S | 10/2019 | Forrest et al. |
| 10,441,181 | B1 | 10/2019 | Telfort et al. |
| 10,441,196 | B2 | 10/2019 | Eckerbom et al. |
| 10,448,844 | B2 | 10/2019 | Al-Ali et al. |
| 10,448,871 | B2 | 10/2019 | Al-Ali et al. |
| 10,456,038 | B2 | 10/2019 | Lamego et al. |
| 10,456,090 | B2 | 10/2019 | Thorpe et al. |
| 10,463,340 | B2 | 11/2019 | Telfort et al. |
| 10,471,159 | B1 | 11/2019 | Lapotko et al. |
| 10,505,311 | B2 | 12/2019 | Al-Ali et al. |
| 10,524,738 | B2 | 1/2020 | Olsen |
| 10,532,174 | B2 | 1/2020 | Al-Ali |
| 10,537,285 | B2 | 1/2020 | Shreim et al. |
| 10,542,903 | B2 | 1/2020 | Al-Ali et al. |
| 10,555,678 | B2 | 2/2020 | Dalvi et al. |
| 10,568,553 | B2 | 2/2020 | O'Neil et al. |
| 10,608,817 | B2 | 3/2020 | Haider et al. |
| D880,477 | S | 4/2020 | Forrest et al. |
| 10,617,302 | B2 | 4/2020 | Al-Ali et al. |
| 10,617,335 | B2 | 4/2020 | Al-Ali et al. |
| 10,637,181 | B2 | 4/2020 | Al-Ali et al. |
| D886,849 | S | 6/2020 | Muhsin et al. |
| D887,548 | S | 6/2020 | Abdul-Hafiz et al. |
| D887,549 | S | 6/2020 | Abdul-Hafiz et al. |
| 10,667,764 | B2 | 6/2020 | Ahmed et al. |
| D890,708 | S | 7/2020 | Forrest et al. |
| 10,721,785 | B2 | 7/2020 | Al-Ali |
| 10,736,518 | B2 | 8/2020 | Al-Ali et al. |
| 10,750,984 | B2 | 8/2020 | Pauley et al. |
| D897,098 | S | 9/2020 | Al-Ali |
| 10,779,098 | B2 | 9/2020 | Iswanto et al. |
| 10,827,961 | B1 | 11/2020 | Iyengar et al. |
| 10,828,007 | B1 | 11/2020 | Telfort et al. |
| 10,832,818 | B2 | 11/2020 | Muhsin et al. |
| 10,849,554 | B2 | 12/2020 | Shreim et al. |
| 10,856,750 | B2 | 12/2020 | Indorf et al. |
| D906,970 | S | 1/2021 | Forrest et al. |
| D908,213 | S | 1/2021 | Abdul-Hafiz et al. |
| 10,918,281 | B2 | 2/2021 | Al-Ali et al. |
| 10,932,705 | B2 | 3/2021 | Muhsin et al. |
| 10,932,729 | B2 | 3/2021 | Kiani et al. |
| 10,939,878 | B2 | 3/2021 | Kiani et al. |
| 10,956,950 | B2 | 3/2021 | Al-Ali et al. |
| D916,135 | S | 4/2021 | Indorf et al. |
| D917,046 | S | 4/2021 | Abdul-Hafiz et al. |
| D917,550 | S | 4/2021 | Indorf et al. |
| D917,564 | S | 4/2021 | Indorf et al. |
| D917,704 | S | 4/2021 | Al-Ali et al. |
| 10,987,066 | B2 | 4/2021 | Chandran et al. |
| 10,991,135 | B2 | 4/2021 | Al-Ali et al. |
| D919,094 | S | 5/2021 | Al-Ali et al. |
| D919,100 | S | 5/2021 | Al-Ali et al. |
| 11,000,645 | B2 | 5/2021 | Estes et al. |
| 11,006,867 | B2 | 5/2021 | Al-Ali |
| D921,202 | S | 6/2021 | Al-Ali et al. |
| 11,024,064 | B2 | 6/2021 | Muhsin et al. |
| 11,026,604 | B2 | 6/2021 | Chen et al. |
| D925,597 | S | 7/2021 | Chandran et al. |
| D927,699 | S | 8/2021 | Al-Ali et al. |
| 11,076,777 | B2 | 8/2021 | Lee et al. |
| 11,114,188 | B2 | 9/2021 | Poeze et al. |
| D933,232 | S | 10/2021 | Al-Ali et al. |
| D933,233 | S | 10/2021 | Al-Ali et al. |
| D933,234 | S | 10/2021 | Al-Ali et al. |
| 11,145,408 | B2 | 10/2021 | Sampath et al. |
| 11,147,518 | B1 | 10/2021 | Al-Ali et al. |
| 11,185,262 | B2 | 11/2021 | Al-Ali et al. |
| 11,191,484 | B2 | 12/2021 | Kiani et al. |
| 11,241,534 | B2 | 2/2022 | Miller et al. |
| D946,596 | S | 3/2022 | Ahmed |
| D946,597 | S | 3/2022 | Ahmed |
| D946,598 | S | 3/2022 | Ahmed |
| D946,617 | S | 3/2022 | Ahmed |
| 11,272,839 | B2 | 3/2022 | Al-Ali et al. |
| 11,289,199 | B2 | 3/2022 | Al-Ali |
| RE49,034 | E | 4/2022 | Al-Ali |
| 11,298,021 | B2 | 4/2022 | Muhsin et al. |
| D950,580 | S | 5/2022 | Ahmed |
| D950,599 | S | 5/2022 | Ahmed |
| D950,738 | S | 5/2022 | Al-Ali et al. |
| D957,648 | S | 7/2022 | Al-Ali |
| 11,376,362 | B2 | 7/2022 | Mazlish |
| 11,382,567 | B2 | 7/2022 | O'Brien et al. |
| 11,386,482 | B2 | 7/2022 | Estes |
| 11,389,093 | B2 | 7/2022 | Triman et al. |
| 11,406,286 | B2 | 8/2022 | Al-Ali et al. |

(56) References Cited

U.S. PATENT DOCUMENTS

| | | | |
|---|---|---|---|
| 11,417,426 | B2 | 8/2022 | Muhsin et al. |
| 11,439,329 | B2 | 9/2022 | Lamego |
| 11,445,948 | B2 | 9/2022 | Scruggs et al. |
| 11,446,439 | B2 | 9/2022 | Mazlish et al. |
| D965,789 | S | 10/2022 | Al-Ali et al. |
| D967,433 | S | 10/2022 | Al-Ali et al. |
| 11,464,410 | B2 | 10/2022 | Muhsin |
| 11,504,058 | B1 | 11/2022 | Sharma et al. |
| 11,504,066 | B1 | 11/2022 | Dalvi et al. |
| 11,511,039 | B2 | 11/2022 | Mazlish et al. |
| D971,933 | S | 12/2022 | Ahmed |
| D973,072 | S | 12/2022 | Ahmed |
| D973,685 | S | 12/2022 | Ahmed |
| D973,686 | S | 12/2022 | Ahmed |
| D974,193 | S | 1/2023 | Forrest et al. |
| D979,516 | S | 2/2023 | Al-Ali et al. |
| D980,091 | S | 3/2023 | Forrest et al. |
| 11,596,363 | B2 | 3/2023 | Lamego |
| 11,627,919 | B2 | 4/2023 | Kiani et al. |
| 11,637,437 | B2 | 4/2023 | Al-Ali et al. |
| D985,498 | S | 5/2023 | Al-Ali et al. |
| 11,653,862 | B2 | 5/2023 | Dalvi et al. |
| D989,112 | S | 6/2023 | Muhsin et al. |
| D989,327 | S | 6/2023 | Al-Ali et al. |
| 11,678,829 | B2 | 6/2023 | Al-Ali et al. |
| 11,679,579 | B2 | 6/2023 | Al-Ali |
| 11,684,296 | B2 | 6/2023 | Vo et al. |
| 11,684,716 | B2 | 6/2023 | Zheng et al. |
| 11,692,934 | B2 | 7/2023 | Normand et al. |
| 11,701,043 | B2 | 7/2023 | Al-Ali et al. |
| D997,365 | S | 8/2023 | Hwang |
| 11,721,105 | B2 | 8/2023 | Ranasinghe et al. |
| 11,730,379 | B2 | 8/2023 | Ahmed et al. |
| D998,625 | S | 9/2023 | Indorf et al. |
| D998,630 | S | 9/2023 | Indorf et al. |
| D998,631 | S | 9/2023 | Indorf et al. |
| D999,244 | S | 9/2023 | Indorf et al. |
| D999,245 | S | 9/2023 | Indorf et al. |
| D999,246 | S | 9/2023 | Indorf et al. |
| 11,766,198 | B2 | 9/2023 | Pauley et al. |
| D1,000,975 | S | 10/2023 | Al-Ali et al. |
| 11,803,623 | B2 | 10/2023 | Kiani et al. |
| 11,832,940 | B2 | 12/2023 | Diab et al. |
| D1,013,179 | S | 1/2024 | Al-Ali et al. |
| 11,872,156 | B2 | 1/2024 | Telfort et al. |
| 11,879,960 | B2 | 1/2024 | Ranasinghe et al. |
| 11,883,129 | B2 | 1/2024 | Olsen |
| D1,022,729 | S | 4/2024 | Forrest et al. |
| 11,951,186 | B2 | 4/2024 | Krishnamani et al. |
| 11,974,833 | B2 | 5/2024 | Forrest et al. |
| 11,986,067 | B2 | 5/2024 | Al-Ali et al. |
| 11,986,289 | B2 | 5/2024 | Dalvi et al. |
| 11,986,305 | B2 | 5/2024 | Al-Ali et al. |
| D1,031,729 | S | 6/2024 | Forrest et al. |
| 12,004,869 | B2 | 6/2024 | Kiani et al. |
| 12,014,328 | B2 | 6/2024 | Wachman et al. |
| D1,036,293 | S | 7/2024 | Al-Ali et al. |
| D1,037,462 | S | 7/2024 | Al-Ali et al. |
| 12,029,844 | B2 | 7/2024 | Pauley et al. |
| 12,048,534 | B2 | 7/2024 | Vo et al. |
| 12,064,217 | B2 | 8/2024 | Ahmed et al. |
| 12,066,426 | B1 | 8/2024 | Lapotko et al. |
| D1,041,511 | S | 9/2024 | Indorf et al. |
| D1,042,596 | S | 9/2024 | DeJong et al. |
| D1,042,852 | S | 9/2024 | Hwang |
| 12,076,159 | B2 | 9/2024 | Belur Nagaraj et al. |
| 12,082,926 | B2 | 9/2024 | Sharma et al. |
| 12,097,352 | B2 | 9/2024 | O'Connor et al. |
| D1,044,828 | S | 10/2024 | Chandran et al. |
| D1,048,571 | S | 10/2024 | Yu et al. |
| D1,048,908 | S | 10/2024 | Al-Ali et al. |
| 12,106,752 | B2 | 10/2024 | Campbell et al. |
| 12,114,974 | B2 | 10/2024 | Al-Ali et al. |
| 12,126,683 | B2 | 10/2024 | Koo et al. |
| 12,127,838 | B2 | 10/2024 | Olsen et al. |
| 12,128,213 | B2 | 10/2024 | Kiani et al. |
| 12,131,661 | B2 | 10/2024 | Pauley et al. |
| D1,050,910 | S | 11/2024 | Al-Ali et al. |
| 12,178,572 | B1 | 12/2024 | Pauley et al. |
| 12,178,581 | B2 | 12/2024 | Telfort et al. |
| 12,178,852 | B2 | 12/2024 | Kiani et al. |
| D1,057,159 | S | 1/2025 | DeJong et al. |
| D1,057,160 | S | 1/2025 | DeJong et al. |
| 12,198,790 | B1 | 1/2025 | Al-Ali |
| 12,200,421 | B2 | 1/2025 | Campbell et al. |
| 12,207,901 | B1 | 1/2025 | Lapotko et al. |
| D1,060,680 | S | 2/2025 | Al-Ali et al. |
| D1,061,585 | S | 2/2025 | Indorf |
| D1,063,893 | S | 2/2025 | DeJong et al. |
| 12,220,207 | B2 | 2/2025 | Telfort et al. |
| 12,235,941 | B2 | 2/2025 | Kiani et al. |
| 12,236,767 | B2 | 2/2025 | Muhsin |
| D1,066,244 | S | 3/2025 | Lim et al. |
| D1,066,672 | S | 3/2025 | Al-Ali et al. |
| 12,246,160 | B2 | 3/2025 | Cardinali et al. |
| D1,068,656 | S | 4/2025 | Trevisan et al. |
| D1,071,195 | S | 4/2025 | Seung |
| D1,072,836 | S | 4/2025 | Indorf |
| D1,072,837 | S | 4/2025 | Ahmed et al. |
| 12,272,445 | B1 | 4/2025 | Kiani |
| 12,296,139 | B2 | 5/2025 | Estes |
| 12,300,375 | B2 | 5/2025 | Nazzaro et al. |
| 12,303,667 | B2 | 5/2025 | Desborough et al. |
| 12,303,668 | B2 | 5/2025 | Mazlish et al. |
| D1,078,689 | S | 6/2025 | Hwang |
| D1,079,020 | S | 6/2025 | Hwang |
| 12,336,796 | B2 | 6/2025 | Al-Ali |
| D1,083,653 | S | 7/2025 | DeJong et al. |
| D1,085,102 | S | 7/2025 | Indorf et al. |
| 12,343,501 | B2 | 7/2025 | Zheng et al. |
| 12,343,502 | B2 | 7/2025 | Mazlish et al. |
| 12,362,596 | B2 | 7/2025 | Barker et al. |
| 12,370,307 | B2 | 7/2025 | Lee et al. |
| 12,370,309 | B2 | 7/2025 | Lee et al. |
| 12,383,166 | B2 | 8/2025 | Desborough et al. |
| 12,390,114 | B2 | 8/2025 | Novak, Jr. et al. |
| D1,092,244 | S | 9/2025 | DeJong et al. |
| D1,093,406 | S | 9/2025 | Indorf et al. |
| D1,094,735 | S | 9/2025 | DeJong et al. |
| D1,095,288 | S | 9/2025 | Lim |
| D1,095,483 | S | 9/2025 | DeJong et al. |
| 12,403,245 | B2 | 9/2025 | Estes et al. |
| 12,403,257 | B2 | 9/2025 | Estes et al. |
| 12,406,760 | B2 | 9/2025 | Zade et al. |
| 12,409,270 | B2 | 9/2025 | Lee et al. |
| 12,427,251 | B2 | 9/2025 | Lee et al. |
| 12,429,141 | B2 | 9/2025 | McLaughlin et al. |
| 12,431,229 | B2 | 9/2025 | Lee et al. |
| 12,433,512 | B2 | 10/2025 | Nazzaro et al. |
| 12,433,524 | B2 | 10/2025 | Al-Ali et al. |
| 12,433,998 | B2 | 10/2025 | O'Connor et al. |
| 12,440,128 | B2 | 10/2025 | Al-Ali et al. |
| 12,440,617 | B2 | 10/2025 | Nazzaro |
| D1,102,622 | S | 11/2025 | Al-Ali et al. |
| 12,478,272 | B2 | 11/2025 | Telfort et al. |
| 12,478,293 | B1 | 11/2025 | Al-Ali et al. |
| D1,106,466 | S | 12/2025 | Avendaño et al. |
| 12,495,967 | B2 | 12/2025 | Muhsin et al. |
| 12,495,999 | B2 | 12/2025 | Al-Ali et al. |
| 12,507,952 | B2 | 12/2025 | Al-Ali et al. |
| 12,521,021 | B2 | 1/2026 | Al-Ali et al. |
| 12,521,506 | B2 | 1/2026 | Yu et al. |
| 2001/0034477 | A1 | 10/2001 | Mansfield et al. |
| 2001/0037083 | A1 | 11/2001 | Hartlaub et al. |
| 2001/0039483 | A1 | 11/2001 | Brand et al. |
| 2002/0010401 | A1 | 1/2002 | Bushmakin et al. |
| 2002/0058864 | A1 | 5/2002 | Mansfield et al. |
| 2002/0133080 | A1 | 9/2002 | Apruzzese et al. |
| 2003/0013975 | A1 | 1/2003 | Kiani |
| 2003/0018243 | A1 | 1/2003 | Gerhardt et al. |
| 2003/0144582 | A1 | 7/2003 | Cohen et al. |
| 2003/0156288 | A1 | 8/2003 | Barnum et al. |
| 2003/0212312 | A1 | 11/2003 | Coffin, IV et al. |
| 2004/0106163 | A1 | 6/2004 | Workman, Jr. et al. |

(56)  References Cited

U.S. PATENT DOCUMENTS

| | | |
|---|---|---|
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0194934 A1 | 8/2008 | Ray et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0098548 A1 | 4/2011 | Budiman et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0208155 A1 | 8/2011 | Palerm et al. |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345663 A1 | 12/2013 | Agrawal et al. |
| 2013/0345921 A1 | 12/2013 | Al-Ali et al. |
| 2014/0107607 A1 | 4/2014 | Estes |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2017/0024748 A1 | 1/2017 | Haider |
| 2017/0251974 A1 | 9/2017 | Shreim et al. |
| 2018/0242926 A1 | 8/2018 | Muhsin et al. |
| 2018/0247712 A1 | 8/2018 | Muhsin et al. |
| 2019/0320906 A1 | 10/2019 | Olsen |
| 2020/0060869 A1 | 2/2020 | Telfort et al. |
| 2020/0111552 A1 | 4/2020 | Ahmed |
| 2020/0113520 A1 | 4/2020 | Abdul-Hafiz et al. |
| 2020/0138368 A1 | 5/2020 | Kiani et al. |
| 2020/0163597 A1 | 5/2020 | Dalvi et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0329983 A1 | 10/2020 | Al-Ali et al. |
| 2020/0329993 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0212397 A1* | 7/2021 | Kaib ................... A61N 1/0476 |
| 2021/0236729 A1 | 8/2021 | Kiani et al. |
| 2021/0236730 A1 | 8/2021 | Lee et al. |
| 2021/0256835 A1 | 8/2021 | Ranasinghe et al. |
| 2021/0275101 A1 | 9/2021 | Vo et al. |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0379282 A1 | 12/2021 | O'Connor et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0168500 A1 | 6/2022 | McCaffrey |
| 2022/0218244 A1 | 7/2022 | Kiani et al. |
| 2022/0218897 A1 | 7/2022 | Nazzaro |
| 2022/0287574 A1 | 9/2022 | Telfort et al. |
| 2022/0288311 A1 | 9/2022 | Lee et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0234066 A9 | 7/2024 | Wiel et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |

(56)  References Cited

U.S. PATENT DOCUMENTS

| 2024/0380246 | A1 | 11/2024 | Moran |
| 2024/0380247 | A1 | 11/2024 | Moran |
| 2024/0404549 | A1 | 12/2024 | Campbell et al. |
| 2025/0000458 | A1 | 1/2025 | Abdul-Hafiz et al. |
| 2025/0037836 | A1 | 1/2025 | Kiani |
| 2025/0100482 | A1 | 3/2025 | Al-Ali et al. |
| 2025/0118415 | A1 | 4/2025 | Olsen |
| 2025/0135114 | A1 | 5/2025 | Bussiere et al. |
| 2025/0144295 | A1 | 5/2025 | Zheng et al. |
| 2025/0205427 | A1 | 6/2025 | Lee et al. |
| 2025/0246285 | A1 | 7/2025 | Alles et al. |
| 2025/0255764 | A1 | 8/2025 | Stead |
| 2025/0278512 | A1 | 9/2025 | Koo et al. |
| 2025/0281059 | A1 | 9/2025 | Avendano |
| 2025/0281078 | A1 | 9/2025 | Desborough et al. |
| 2025/0281688 | A1 | 9/2025 | Estes |
| 2025/0288250 | A1 | 9/2025 | Al-Ali et al. |
| 2025/0295366 | A1 | 9/2025 | Al-Ali et al. |
| 2025/0302426 | A1 | 10/2025 | Ha et al. |
| 2025/0311949 | A1 | 10/2025 | Al-Ali et al. |
| 2025/0318761 | A1 | 10/2025 | Al-Ali et al. |
| 2025/0319257 | A1 | 10/2025 | Mazlish et al. |
| 2025/0322950 | A1 | 10/2025 | Al-Ali et al. |
| 2025/0323417 | A1 | 10/2025 | Rey |
| 2025/0329240 | A1 | 10/2025 | Kiani |
| 2025/0344010 | A1 | 11/2025 | Al-Ali et al. |
| 2026/0014333 | A1 | 1/2026 | Fernkvist et al. |
| 2026/0014334 | A1 | 1/2026 | Danwihl |

OTHER PUBLICATIONS

Ellingsen et al., "Safety Constraints in an Artificial Pancreatic β Cell: An Implementation of Model Predictive Control with Insulin on Board", Journal of Diabetes Science and Technology, vol. 3, No. 3, May 2009, pp. 536-544.

* cited by examiner

FRONT VIEW                    ANGLED VIEW

FRONT VIEW          ANGLED VIEW

806

802

816

804

818

808          810          812          814

802

818

804

810          816

MODULAR WEARABLE DEVICE FOR PATIENT MONITORING AND DRUG ADMINISTRATION

INCORPORATION BY REFERENCE TO ANY PRIORITY APPLICATIONS

The present application claims a priority benefit under 35 U.S.C. § 119(e) to Provisional Pat. App. No. 63/300,426, filed Jan. 18, 2022, entitled "MODULAR WEARABLE DEVICE FOR PATIENT MONITORING AND DRUG ADMINISTRATION," which is incorporated by reference herein.

BACKGROUND

Field

The present application relates generally to the field of wearable sensor devices and drug treatment systems.

Description of the Related Art

The management of various diseases, such as diabetes, may include the measurement of analyte within the interstitial space including blood and/or interstitial fluid of a patient and administration of drug to the patient. A closed loop drug administration system includes both a sensor to take analyte measurements from the interstitial space including blood and/or interstitial fluid of the patient and a drug administration device which administers drug to the patient based on the analyte measurements. Considering diabetes treatment, closed-loop insulin administration systems allow individuals impacted by diabetes to go about daily life with much less worry about their insulin and/or glucose levels, which can vastly improve their quality of life.

SUMMARY

In one aspect, the present disclosure provides a modular wearable device for patient monitoring and drug delivery, the modular wearable device including: a fastening portion that can removably affix the modular wearable device to a portion of a patient; and a plurality of module receiving portions that can receive removable modules, where a first removable module comprises a physiological sensor and a second removable module comprises a drug delivery reservoir.

In some embodiments, the modular wearable device can removably affix to at least one of: the patient's arm, the patient's leg, the patient's waist, or the patient's chest.

In some embodiments the module receiving portions can accept, hold, and release the removable modules.

In some embodiments, the module receiving portions can receive a third removable module including a battery, the device including a power connection between the battery and at least one other removable module.

In some embodiments, the module receiving portions can receive a third removable module including a wireless module.

In some embodiments, the wireless module comprises at least one of: an optical transceiver, an acoustic transceiver, a Bluetooth transceiver, a GPS transceiver, a Wi-Fi transceiver, or a wireless broadband transceiver. In some embodiments, the physiological sensor comprises an external detector that can removably affix to the patient.

In some embodiments, the physiological sensor comprises at least one of: an analyte sensor, an inertial measurement sensor, a skin impedance sensor, a microphone, a haptic sensor, an optical sensor, a pulse measurement sensor, a diffuse reflectance sensor, or a Raman sensor.

In some embodiments, the analyte sensor comprises at least one of: a glucose sensor, a lipid sensor, a lactic acid sensor, a ketone sensor, an oxygen sensor, or a carbon dioxide sensor.

In some embodiments, the drug delivery reservoir comprises insulin, hyaluronidase, or an analgesic.

In some embodiments, the drug delivery reservoir comprises a drug pump.

In some embodiments, the drug delivery reservoir can deform. In some further embodiments, the drug delivery reservoir can deform as a liquid drug is dispersed.

In some embodiments, the modular wearable device comprises a fluid channel can inject a liquid drug into the patient. In some further embodiments, the fluid channel can resist deformation.

In some embodiments, the modular wearable device comprises a second fluid channel connecting at least two drug delivery reservoirs. In some further embodiments, the second fluid channel can mix liquid drug from the at least two drug delivery reservoirs. In some further embodiments, the second fluid channel can resist deformation.

In some embodiments, the modular wearable device comprises a signaling connection between the physiological sensor and at least one other module.

In some embodiments, the modular wearable device comprises a flexible material that can conform to an attachment site on the patient.

DETAILED DESCRIPTION

Figures 1A, 1B:
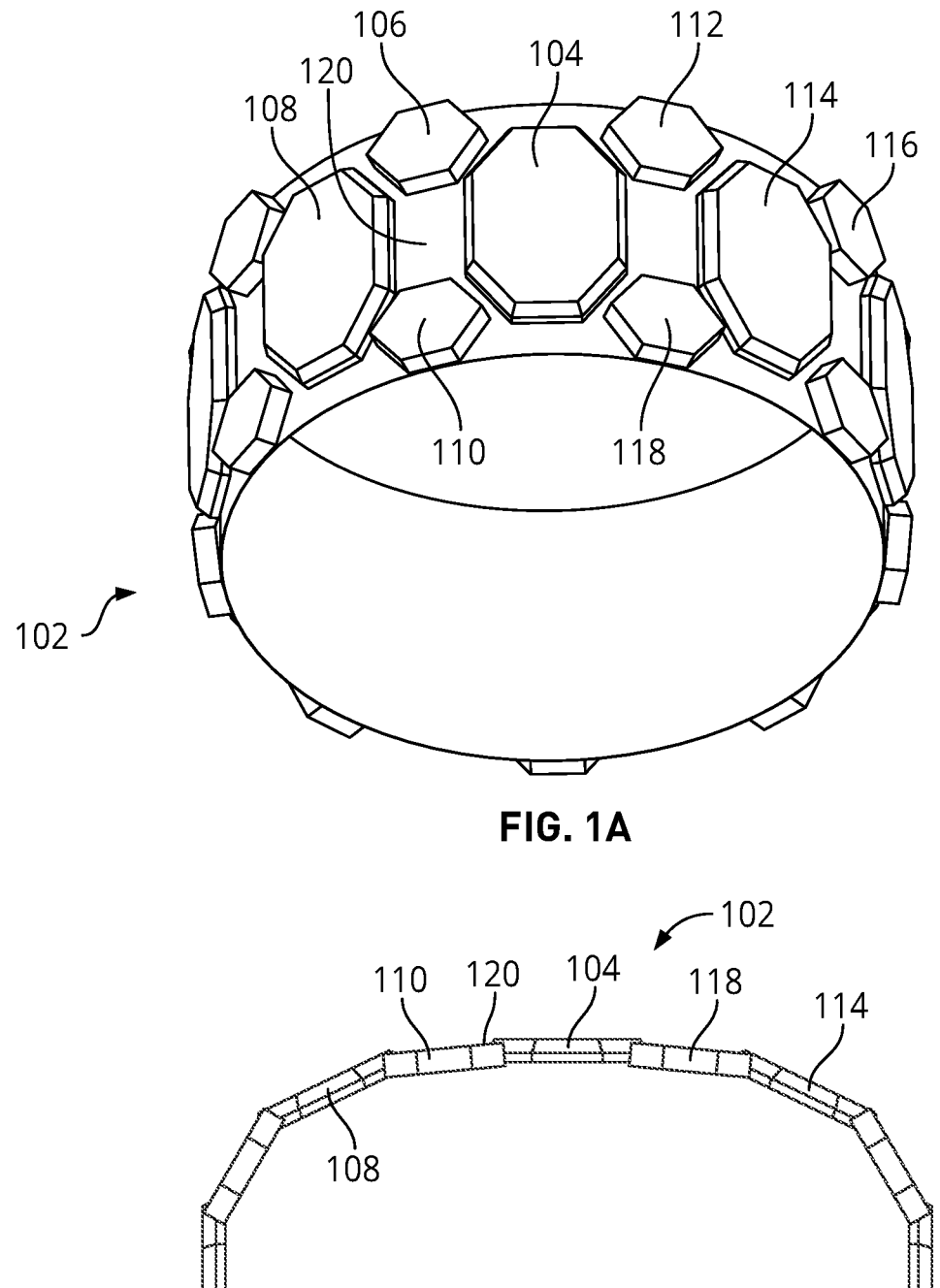
FIG. 1A illustrates, from a front view, an example modular wearable device having several removable modules.
FIG. 1B illustrates, from a bottom view, an example modular wearable device having several removable modules.

Aspects of the disclosure will now be set forth in detail with respect to the figures and various examples. One of skill in the art will appreciate, however, that other embodiments of the devices and methods disclosed herein will still fall within the scope of this disclosure even if not described in the same detail. Aspects of various embodiments discussed do not limit the scope of the disclosure herein, which is instead defined by the claims following this description.

Two factors may prevent users from carrying more insulin in patch pumps currently: (1) infusion cannulas limit use to three days and (2) ultra-rapid-acting insulin has a maximum concentration of U100. There are very few U200 insulin vendors and U200 tends to be more expensive. As such, there has not been a great need to hold more than 3 mL of insulin.

Systems and methods described herein relate to a modular wearable device that can allow for more extended use of monitoring and/or disease management devices, such as a continuous glucose monitor, insulin pump, and/or other minimally invasive device. For example, a disease management device, such as an insulin pump, or other minimally invasive device may require periodic replacement of components or the entire device every few days to reduce the risk of infection or refresh a medication supply. With the use of a modular wearable device, such as described herein, a user may be able to replace components of the device as needed without entirely replacing the device, easing use of the system and prolonging wear time of the modular wearable device. Prolonged wear time may be beneficial because it can require fewer interactions of the user with the device and calibrations of the device. Such a device may also enable easy introduction of new modular systems that may upgrade performance of the device. Additionally, the modular system may allow the user to use multiple sensors and/or medication delivery modules as part of the same device, simplifying use and management of disease management systems for that user.

Systems and methods described herein may be applicable to various patient conditions, such as diabetes, that may be treated with an implant or other minimally invasive or non-invasive device that can monitor a patient state and deliver medication on an ongoing or temporary basis. While reference may be made to a specific disease, such as diabetes, systems and methods described herein may be applicable to other diseases and conditions.

While in some examples, systems and methods described herein may reference monitoring and/or sensing of a specific parameter and/or blood analyte, such as glucose, other physiological conditions, physiological states, physiological parameters, physiological markers, blood analytes, the like or a combination thereof may be monitored or determined in addition or in the alternative to glucose. Similarly, while in some examples, reference may be made to a specific type of sensor, such as a glucose sensor, other analyte sensors may additionally or alternatively be used. For example, in some embodiments, a glucose sensor can measure other analytes. Additionally or alternatively, while reference may be made to specific types of invasive or non-invasive sensors, for example an invasive glucose sensor, any type of invasive or non-invasive sensor may be used, such as a non-invasive analyte sensor.

Additionally or alternatively, while in some examples, systems and methods described herein may reference specific medication, such as insulin, hyaluronidase, or an analgesic, to be delivered to the patient, other medications, fluids, or treatments may be administered in addition or in the alternative to those medications. Similarly, the components described herein may be used with any fluid or medication. Multiple forms of medication or mixtures of medication can be stored in drug delivery reservoirs for later mixing in a co-formulated dosing or connected to separate pump elements on the modular wearable device.

Overview of an Example Modular Wearable Device

Systems and methods described herein may include a modular wearable device that can receive and use modules. The modules may be associated with one or more sensors, medication delivery devices and/or other disease management devices. The modular wearable device can be removably worn by a user or patient. The modular wearable device may include some combination of flexible and rigid material so as to allow the user or patient to attach at least a portion of the modular wearable device to a body part, such as a wrist, ankle, waist, other area of the abdomen, other area of the leg, other area of the arm, or other area of the body. Unobtrusive wear of the modular wearable device may improve patient comfort and enable long-term usage of the modular wearable device. Low-profile, thin, and/or flexible removable modules may help achieve unobtrusive wear for the patient.

FIGS. 1A and 1B illustrate views of a non-limiting example of a modular wearable device 102 that may can be removably worn by a patient. In the illustrated example, a modular wearable device 102 includes a flexible material 120 and module receiving portions to which one or more removable modules 104, 106, 108, 110, 112, 114, 116, and 118 may be attached. The device may be worn by a patient. A flexible material 120 may facilitate conformation of the device to the shape of the patient's body at an attachment site.

The flexible material 120 may facilitate conformation of the device to the shape of the patient's body at an attachment site. The flexible material 120 may be at least between module receiving portions or modules 104, 106, 108, 110, 112, 114, 116, and 118. In some examples, the module receiving portions may include at least some of the flexible material 120. The flexible material 120 may include a silicone, a leather, a plastic, an elastane, another material, or a combination thereof. In some examples, the flexible material 120 may be a semi-rigid material or structure that can conform or approximately conform to the patient's body at the attachment site. For example, the material may be a rigid material formed as a chain, linked, and/or woven to allow flexibility of movement of the device around the attachment site. In some examples, the flexible material may include at least some rigid portions and can at least partially conform to the attachment site of the patient.

Figure 2:
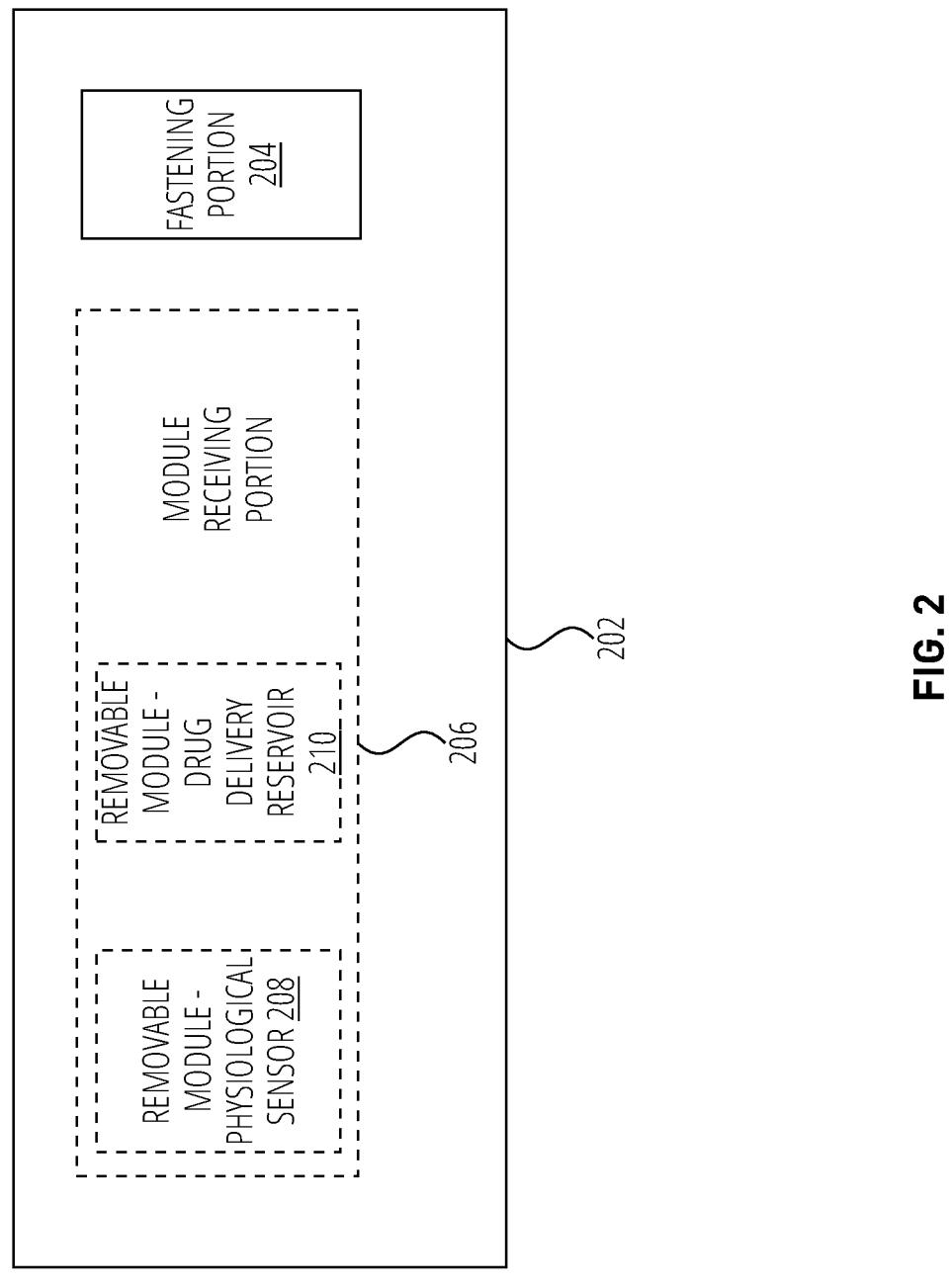
FIG. 2 schematically illustrates a block diagram of example components of a modular wearable device.

FIG. 2 schematically illustrates a block diagram of an example modular wearable device, such as illustrated in FIGS. 1A and 1B. In the example of FIG. 2, the modular wearable device 202 may include a fastening portion 204, module receiving portions 206, and removable modules 208 and 210. In some examples, the removable modules 208 and 210 may reversibly couple and/or reversibly attach to the modular wearable device 202. The removable module 208 may include, for example, a physiological sensor while removable module 210 may include a drug delivery reservoir. Either of removable modules 208 or 210 may be detached from the module receiving portion on which it sits. When detached, removable modules 208 or 210 may be reattached to any unoccupied module receiving portion 206.

The physiological sensor of the removable module 208 may be used to sense some physiological parameter of the patient. The physiological sensor of the removable module 208 may, for example, connect to an external detector for purposes of measuring and/or communicating sensing data. The removable module 210 may include a liquid drug reservoir and/or a drug pump. The drug delivery reservoir and/or the drug pump may be used to store and/or administer liquid drug to the patient. The removable modules 208 and/or 210 may connect to other modules via signaling connections or power connections. The removable module 210 may connect to other modules by fluid channel. The fastening portion 204 may be used to secure the modular wearable device 202 to a patient.

Herein are provided approaches for mounting sensors and/or large volumes of drug, such as insulin, on a patient's body via a modular wearable device. Such a modular wearable device may be useful to a patient desiring to be mobile but also needing monitoring and/or drug administration over an extended period of time. Advantageously, the modular wearable device may be both flexible and/or thin on the patient's body, facilitating comfortable, unobtrusive wear while also allowing the patient to carry large amounts of drug and/or one or more sensors. Comfortable wear may help a patient wear the device for the extended period of time.

The modular aspect of the device allows for ease of use. For example, the modular design allows for quick, easy placement and replacement of modules including drug reservoirs and/or sensors, or other modules including, for example, batteries. Easy component replacement may allow the patient to wear the device for a long period of time relative to other systems because certain components can be quickly replaced rather than having to remove the entire device. For example, if a drug reservoir runs low on liquid drug, the module including that drug reservoir may be removed and replaced with a fresh, full drug reservoir while a patient wears the modular device. Or, as another example, if a battery module runs low on charge, that battery module may be quickly swapped for a battery module having a full charge while other modules remain attached to the modular wearable device. In some examples, modules on a modular wearable device may be removable to allow the reuse of expensive components on a disposable adhesive device fixture.

A status of one or more modules may be indicated to a patient or user via an alert. The alert may be audible, visual, tactile, or a combination thereof. The modular wearable device may include one or more hardware processors that can determine the status of one or more modules. The hardware processor may be capable of generating the alert. The one or more hardware processors may be in communication with the one or more modules. Additionally or alternatively, the one or more hardware processors may be part of the one or more modules. In some examples, the one or more hardware processors can determine disease management parameters, physiological parameters, control signals, or a combination thereof. The one or more hardware processors may be in communication with a user device, such as a smart watch, smart phone, other personal computing device, patient monitoring device, the like or a combination thereof. The one or more hardware processors can communicate with a remote computing device or the cloud. In some examples, the one or more hardware processors may receive information from a secondary device in order to operate aspects of the wearable device or assist the user in operation of the modular wearable device.

Additionally, the modular aspect of the device facilitates customization of the device. For example, it may be the case that a first patient needs a particular set of sensor modules and/or drug administration modules while a second patient needs a different set of sensor modules and/or drug administration modules. Because the modular wearable device allows for attachment of a variety of different modules, the first and second patients could each use their own modular wearable device and simply attach their respective relevant sets of modules.

For example, FIG. 1A and FIG. 1B illustrate examples of removable module geometries that may enable flexion of the modular wearable device across a patient. Modular wearable device 102, shown from the front in FIG. 1A, may be include several removable modules, including, for example, 104, 106, 108, 110, 114, and 116.

The removable modules 104, 106, 108, 110, 114, and 116 may be unobtrusive, having a profile that does not extend far outward from the patient. Additionally, removable modules 104, 106, 108, 110, 114, and 116 may substantially conform to a curvature of the attachment site of the patient. The removable modules, for example 108, 110, 104, 114, and 118 may be unobtrusive. In some examples, removable modules 104, 106, 108, 110, 114, and 116 may have a narrow profile such that the flexible material 120 of the modular wearable device 102 may still conform to the curvature of the patient at the attachment site. Some removable modules, for example 106, 112, 116, and 118, are smaller than others, for instance 104, 108, and 114. Difference in sizing may allow many different modules to fit on the modular wearable device 102 while enabling flexion of the device around the site of attachment. In certain examples, removable modules 104, 106, 108, 110, 114, and 116 may include flexible material such that the modules themselves may substantially conform to the curvature of the attachment site of the patient.

An example modular wearable device 102, shown from the bottom in FIG. 1B, illustrates that the removable modules, for example 108, 110, 104, 114, and 118 may have a slim profile that may not extend far from the body of a patient wearing modular wearable device 102. Further, the removable modules, for example 104 and 114, may be spaced such that there may be portions of the modular wearable device 102, for example region 120, where the modular wearable device 102 is not covered by a removable module. The region 120 may include flexible material, enabling flexion.

Such a device may enable easy attachment of new modular systems that could upgrade performance of a closed loop algorithm. These may include new modalities of noninvasive and invasive sensors such as those discussed below. Other sensing technologies may be incorporated in such a device include, for example: phase conjugate spectroscopy, diffuse reflectance, diffuse transmission, anti-Stokes Raman spectroscopy, Stokes Raman spectroscopy, coherent Raman spectroscopy, fluorescence, temperature, skin impedance, accelerometers, gyroscopes, spirometers, biochemical assays, or impedance spectroscopies. Other sensing technologies may be incorporated into the device. Sensing technologies may be incorporated in a non-contact method, minimally invasive method, invasive method, and/or non-invasive method.

Module Receiving Portions

In some examples, the modular wearable device may include one or more module receiving portions to attach various removable modules. In some examples, module receiving portions may integrate with connectors that support multiple module types including optical sensor, electrical power, medication storage, wireless modules, or others. Example mechanisms by which the removable module may removably attach to a module receiving portion are discussed herein.

Figure 3:
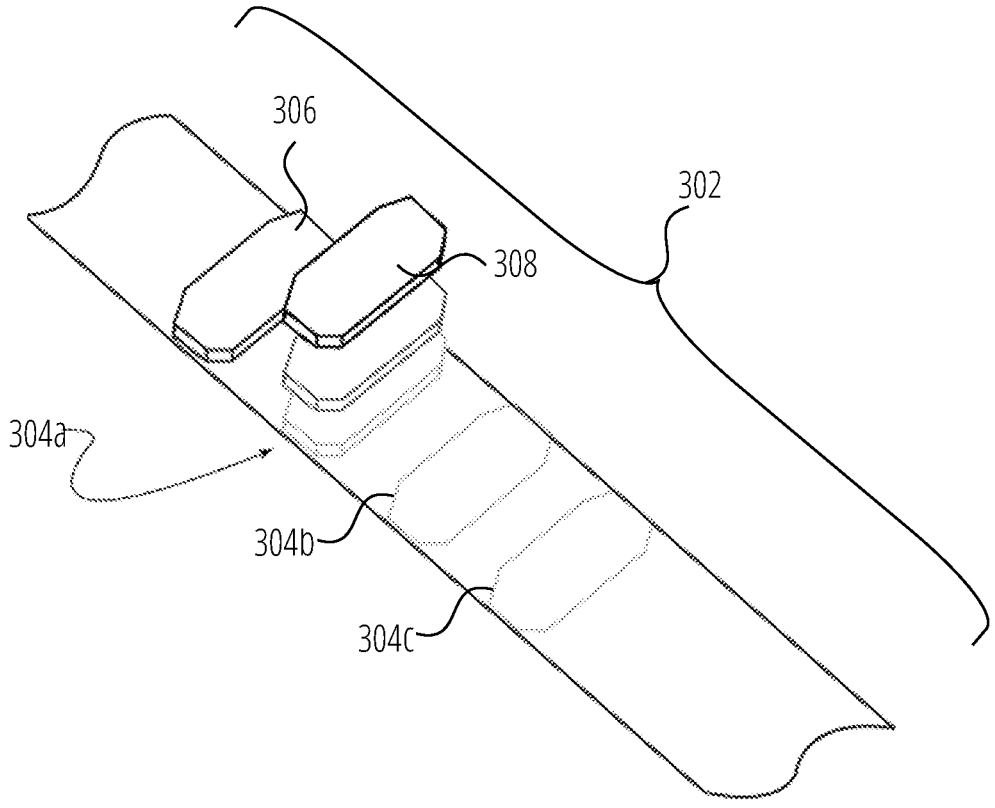
FIG. 3 illustrates one example of a modular wearable device having module receiving portions that can accept and hold removable modules on the modular wearable device.

With continued reference to FIGS. 1A and 1B, the one or more removable modules 104, 106, 108, 110, 112, 114, 116, and 118 may be of the same size and shape or different size and shape. The one or more removable modules 104, 106, 108, 110, 112, 114, 116, and 118 can attach to module receiving portions specific to the type of removable module or generic to the type of removable module. For example, the one or more removable modules may have one or more connections points or connectors that can attach to one or more connection points or connectors on the module receiving portions. In some examples, one or more of the connection points or connectors may be oriented the same across modules and module receiving portions so as to allow for different module receiving portions to receive the same module and/or the same module receiving portion to receive different modules. In some examples, the module receiving portions may be specific to a specific module or a specific type or types of module, such as a medication delivery module, non-invasive sensor, or minimally invasive sensor. As an illustrative example, a first type of module receiving portion can receive a plurality of different non-invasive sensor modules, a second type of module receiving portion can receive a plurality of different medication delivery modules, a third type of module receiving portion can receive minimally invasive sensor modules. In some examples, a module receiving portion can allow access of at least a portion of the module to a tissue site of the patient. For example, a module receiving portion may include one or more openings to allow a sensor or catheter direct access to the tissue of the patient. FIG. 3 illustrates an example of a modular wearable device having module receiving portions. In the illustrated example, the modular wearable device 302 includes module receiving portions 304, and removable modules 306 and 308. Removable module 308 may be affixed to any of the module receiving portions 304. As illustrated, the removable module 308 may be placed, for instance, on a module receiving portion 404 closest to removable module 306. The removable modules 306 and 308 may also be removed as desired. The module receiving portions 304 can, but need not, receive a module. For example, as in the diagrammed example, the two module receiving portions 304b and 304c are not attached to a removable module. However, in some examples, each module receiving portion may be occupied by a removable module during use.

The module receiving portions may include at least one attachment mechanism for securing a module into a module receiving area of the module receiving portion. An attachment mechanism can secure the module during normal use to the module receiving portion. Normal use may include, but is not limited to, wear of the modular wearable device during a period of hours or days. The attachment mechanism may allow the user to detach a module from a module receiving portion when desired. In some examples, the attachment mechanism may include a clip, hook and loop, snap, other semi-permanent or temporary attachment mechanism, the like or a combination thereof. In some examples, the attachment mechanism may be reusable, allowing for attachment or coupling of at least one module to the module receiving portion repeatedly. In some examples, the attachment mechanism may be specific to a specific module or specific type or types of modules. In some examples, the attachment mechanism may be the same for different modules (e.g., the attachment mechanism may be non-specific).

In some examples, a removable module may have an adhesive on the entirety of the surface that faces the module-receiving portion of the device. For example, a hook-and-loop fastening surface may cover a surface of a removable module enabling attachment to a module-receiving portion having a complementary hook-and-loop surface. In some examples, a removable module may attach to a module-receiving portion at anchor points. For example, a module may have one or more snap fastener attachments at one or more anchor points that can interface with a corresponding number of fastener attachments at corresponding anchor points on the module receiving portion.

In some examples, the module receiving portions may be pliable and/or flexible. In other examples, the module receiving portion may be stiff. In these examples, the module receiving portions may include a shell. The shell may be shaped to conform to a surface of a module. The attachment surface may be on the shell.

Figure 4:
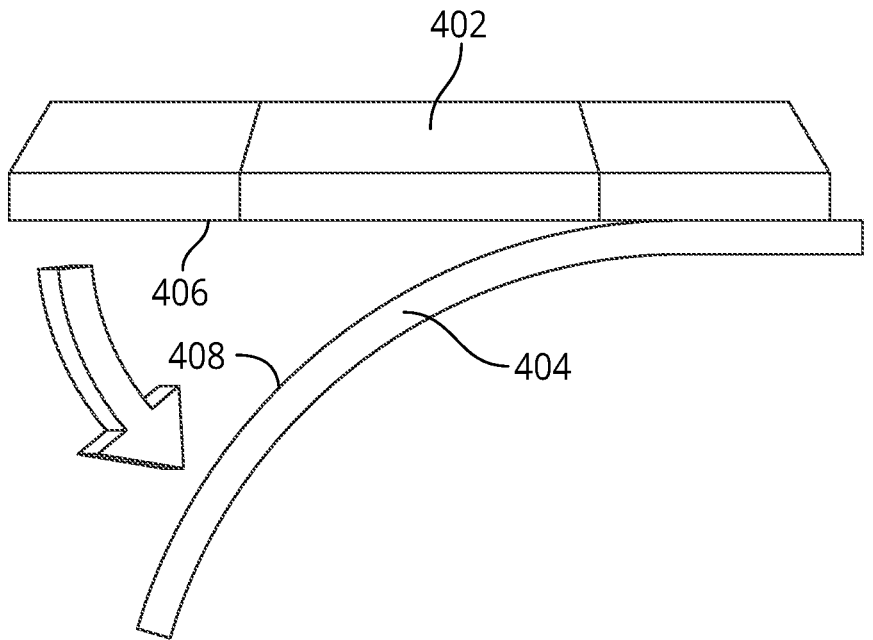
FIG. 4 illustrates one example mechanism by which a removable module may attach to a module receiving portion.

FIG. 4 diagrams one example attachment mechanism of a removable module 402 and a removable module receiving portion 404. In the illustrated example, a removable module 402 may have a first adhesive surface 406 attaching to a module receiving portion 404 having a second adhesive surface 408. The first adhesive surface 406 covers the downward-facing surface of the removable module 402. Removable module 402 and the module receiving portion 404 may be removably attached to each other by contacting adhesive surfaces 1206 and 408 together. Adhesive surfaces 406 and 408 may be, for example, a hook and loop fastener system. Adhesive surfaces 406 and 408 may include any other adhesive sufficient to attach a removable module. Removable module 402 and module receiving portion 404 may be detached from each other by peeling the first adhesive surface 406 of the removable module 402 from the second adhesive surface 408 of the module receiving portion 404.

Removable Modules

Removable modules may include, but are not limited to, sensors and/or disease management devices, such as medication delivery pumps or the like. In some examples, removable modules may include electronic components, such as battery systems, wireless communication systems, a display system, the like or a combination thereof.

In some examples, removable modules may be mounted such that they are freely held by the modular wearable device, having little or no close body contact on portions of the removable modules. Mechanisms to enable removable modules to be freely held may include a bracket or a track. In some examples, removable modules may include a portion that has close body contact so that a patient contact component of the removable module may have access to a tissue site. A patient contact component may include, but are not limited to, a sensor, sensor probe, catheter, the like or a combination thereof.

In some examples, multiple removable modules may be worn simultaneously. In some examples, removable modules may be placed to spread the load across the wearable device. In some examples, a single removable module may be worn on the wearable device. In some examples, one or more removable modules may be placeholder modules that can spread the weight more evenly across the wearable device when wearing an uneven number of active removable modules on the wearable device. Placeholder modules may not include components relating to drug delivery or parameter sensing. Placeholder modules may have a similar shape, size, and/or weight to the active removable modules.

Figure 5:
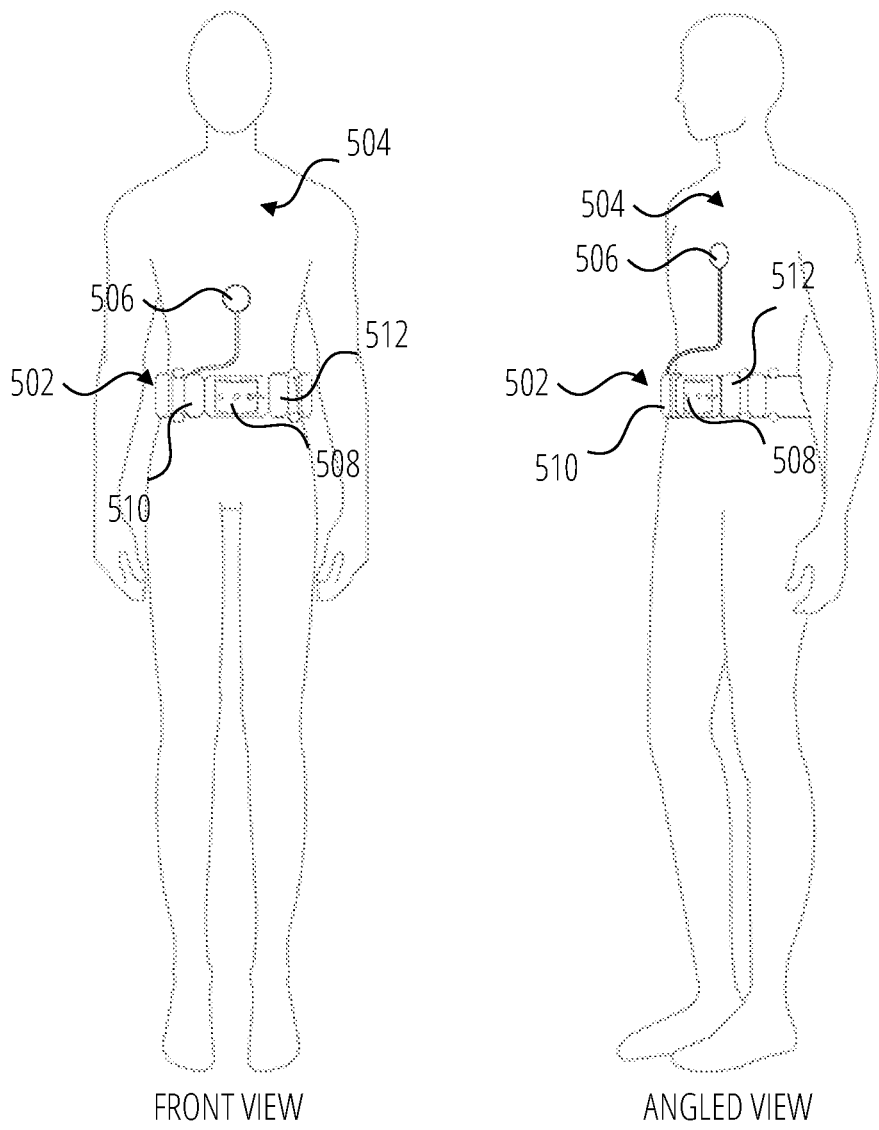
FIG. 5 illustrates one example of the modular wearable device, wherein the modular wearable device can removably affixed to a patient's waist.
Figure 6:
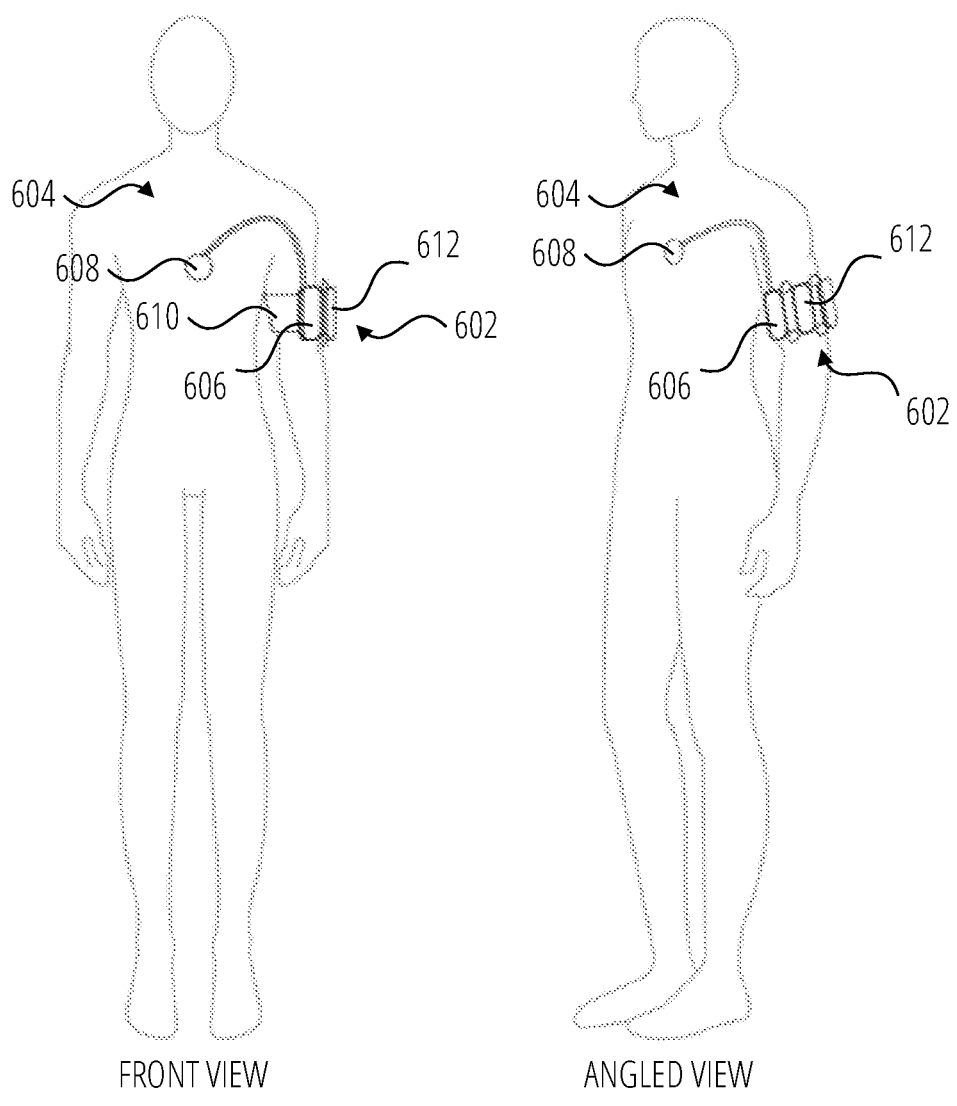
FIG. 6 illustrates one example, wherein the modular wearable device is can be removably affixed to a patient's arm.

While reference may be made to the use of a certain number or type of removable modules, any combination and number of modules may be used, such as one, two, three, four, five, six, seven, eight, nine or more redundant or different modules. In some examples, redundant devices may be used to manage aspects of a patient's health, such as two identical drug delivery reservoirs or two identical physiological sensors. In some examples, different modules may be used and in communication to manage different aspects of a patient's health or different aspects of disease management, such as a drug delivery reservoir and analyte sensor.
Securing the Modular Wearable Device to the Patient In some examples, the wearable module device may be removably secured around a portion of the patient's body. In some examples, the wearable modular device may be secured around the patient's waist, the patient's chest, the patient's arm, or the patient's leg. Other attachment sites may also be suitable. FIGS. 5 and 6 illustrate examples of a user wearing a wearable module device on attachment sites at the abdomen and arm respectively.

In the example illustrated in FIG. 5, the system includes a modular wearable device 502 that may be worn by a patient 504. In one example, as illustrated in FIG. 5, the patient 504 may wear the modular wearable device 502 around the waist. The modular wearable device 502 includes a fastening portion 508, a sensor module 510, an external detector 506, and a removable module 512. The fastening portion 508 may be used to removably affix the modular wearable device 502 to the patient 504. The fastening portion 508 may be adjusted for a comfortable fit. The fastening portion 508 diagrammed in FIG. 5 is a belt buckle, but the fastening portion may be any suitable fastening mechanism, for example: an elastic strap, a belt buckle, a hook and loop fastener, a tie, a zipper, a hole and button, a toggle, a snap fastener, a grommet, a magnet, or a cord lock.

The sensor module 510 may be connected to an external detector 506 such that information measured by the external detector 506 may be communicated to the sensor module 510. The external detector 506 may be noninvasively, minimally invasively, or invasively affixed to the patient 504. The external detector 506 may be removable from the patient 504 on a regular basis, semi-removable, or permanent. The sensor module 510 and removable module 512 sit upon module receiving portions and may be removed from the modular wearable device 502. Once removed, either the sensor module 510 or the removable module 512 may be reaffixed to the modular wearable device 502 at a module receiving portion.

In the example illustrated in FIG. 6, the patient 604 may wear the modular wearable device 602 around the arm. The modular wearable device 602 includes a fastening portion 610, a sensor module 606, an external detector 608, and a removable module 612. The fastening portion 610 may be used to removably affix the modular wearable device 602 to the patient 604. The fastening portion 610 may be adjusted for a comfortable fit. The fastening portion 610 diagrammed in FIG. 6 is an elastic strap, but the fastening portion may be any suitable fastening mechanism, for example: an elastic strap, a belt buckle, a hook and loop fastener, a tie, a zipper, a hole and button, a toggle, a snap fastener, a grommet, a magnet, or a cord lock.

The sensor module 606 may be connected to external detector 608 such that information measured by the external detector 608 may be communicated to sensor module 606. The external detector 608 may be noninvasively, minimally invasively, or invasively affixed to the patient 604. The external detector 608 may be removable from the patient 604 on a regular basis, semi-removable, or permanent. The sensor module 606 and the removable module 612 sit upon module receiving portions and may be removed from the modular wearable device 602. Once removed, either the sensor module 606 or the removable module 612 may be reaffixed to the modular wearable device 602 at a module receiving portion.

Example Module Materials

In some examples, removable modules may include some combination of rigid and flexible materials. In some examples, woven flexible material may be used to reinforce and prevent breakage of pressurized soft module compartments while full. A permanent, semipermanent, or temporary chemical or heat-treated adhesion to a material of low melting points may allow external reinforcement of a module. Example materials having a sufficiently low melting point include, but are not limited to, CoC or CoC-amide. External reinforcement may apply to any of the module surface facing the patient's body and those in contact with air facing outward from body. A uniform enclosure of the woven mesh may be advantageous to prevent high stress points in the reinforced compartment while under it experiences high pressure, such as when the patient rolls over or falls on a modular wearable device.

In some examples, a removable module may include a material that may be collapsible and/or include a geometry that allows the removable module to collapse and/or deform. For example, a removable module may include a drug reservoir. At least the drug reservoir or portion of the drug reservoir may be collapsible, capable of collapse, and/or deformable as or after drug has been dispensed. Advantageously, collapsibility and/or deformability may allow liquid drug to be removed from connected removable modules under negative pressure. In some examples, the fluid channels may resist deformation. In some examples, the fluid channels may be more resistant to collapse than the reservoirs. In some examples, a fluid channel may be sufficiently rigid and sufficiently small to enable continuous pumping without notice by the user even if experiencing pressure, for instance, if the patient rolls over on the fluid channel. Various channel lengths, diameters, and/or material hardnesses may be chosen such that the fluid channel may remain unobtrusive to the patient even when the fluid channel experiences exterior pressure, for example, if the patient rolls over onto the fluid channel. In some embodiments, a liquid drug pump can detect or adapt to changes in pressure within the drug reservoir or fluid channel.
Module Linkage Via Fluid Channels It may be advantageous to connect two or more removable modules via fluid channels. For example, connection by fluid channel may allow the mixing of two drugs that cannot be stored together prior to administration. Fluid channels may include the same material as used for the reservoir itself and may include additional reinforcements from woven or other external material. Fluid channels may also include tubing. In some examples, tubing material includes polytetrafluoroethylene (PTFE), expanded PTFE (ePTFE), silicone, platinum cured silicone, or CoC. Other materials may be used, however. In some examples, fluid channels may be one continuous form with drug reservoir modules, overmolds on hardened module materials, or of a detachable form. To attach to drug reservoirs, detachable fluid channels may utilize puncturable septums, press-fit seals, luer locks, or screw-in seals with o-rings.

Hardware Components of Removable Modules

In some examples, a hardware component, such as a drug pump or a sensor, may be included in a single removable module or distributed across two or more removable modules attached to a wearable modular device. In some examples, the pump and cannula insertion may be linked to a drug reservoir, such as an insulin storage compartment, as described below. In some examples, a single removable module may integrate two or more hardware components. For example, a sensor module may have a microphone and a light emission source.

In some examples, the modular wearable device may include removable modules, including but not limited to, an accelerometer, a microphone, a speaker, a haptic sensor, a lighting source, a pulse measurement sensor, a diffuse reflectance sensor, a Raman spectrographic sensor, or others. Module receiving portions may provide nodes connected by flex circuits to a centralized system on a chip (SoC) compartment that include connectors for a modular and upgradeable wearable device. Advantageously, connectivity between two or more removable modules may facilitate a closed-loop, non-invasive approach to a blood-glucose monitoring and administration system, or other similar systems.

In some examples, certain components such as a SoC or a battery may be connected to two or more modules. Other electronic components may additionally or alternatively be connected to two or more modules.

Types of Removable Modules

Drug Delivery Modules

Inclusion of a drug delivery reservoir in the device may advantageously allow for administration of a drug to the patient. In some examples, fluid channels may connect module compartments to a drug pumping or drug insertion module, which enables the administration of liquid drug to the patient. A drug reservoir module may also administer drug directly. In some examples, a drug pump may be integrated into a drug reservoir module. In some examples, a drug pump and a liquid drug compartment are integrated into a drug reservoir module. As an illustrative example, for use by a diabetes patient, it may be desirable for a patch-based insulin pump to hold 6 mL insulin or more at U100 concentration for a period of 7 days or more. Other volumes, concentrations, and durations may be desirable.

Drug reservoir modules may be removed from the modular wearable device for reuse and/or refill. Additionally or alternatively, drug reservoir modules may be attached to drug reservoir modules and may or may not be refillable or reusable.

In some examples, a drug reservoir module may store up to approximately 50 mL of liquid drug, up to approximately 45 mL of liquid drug, up to approximately 40 mL of liquid drug, up to approximately 35 mL of liquid drug, up to approximately 30 mL of liquid drug, up to approximately 25 mL liquid drug, up to approximately 20 mL liquid drug, up to approximately 15 mL liquid drug, up to approximately 10 mL liquid drug, up to approximately 5 mL liquid drug, up to approximately 4 mL liquid drug, up to approximately 3 mL liquid drug, up to approximately 2 mL liquid drug, or up to approximately 1 mL liquid drug, or any value or range within or bounded by any of these ranges or values, although values outside these values or ranges can be used in some cases. Additionally or alternatively, in some examples a drug reservoir module may store up to approximately 6 mL of liquid drug.

In some examples, one or more modules of the modular wearable device can hold multiple medication reservoirs of different types. The multiple medication reservoirs may be stored in different modules or compartments or the same module or compartment before administration to a patient. A single module including two or more liquid drug compartments may store two or more liquid drugs separately. For example, it may be desirable for insulin and hyaluronidase to be stored separately to prevent the hyaluronidase from destabilizing from exposure to insulin preservatives. In some examples, insulin and hyaluronidase can be stored separately before being combined at the time of administration to the patient. Advantageously, separate storage of liquid drugs may enable administration of different amounts of each type to of drug where multiple pumps are used to draw the various medications to a cannula compartment. A user could set pumping rate of the pumps so a desired, different amount of each drug may be administered. In some examples, a removable module may enable mixing of multiple input medications before administration, for example by connecting with fluid channels from separate drug reservoirs. The size of such a module may affect residence time and expected mixing and/or diffusion of the two or more input medications into each other.

In some examples, two or more drug reservoirs may connect to a single cannula to enable administration to the patient. In some examples, liquid drugs from drug reservoirs connected to a single cannula may not mix before administration to the patient. For example, liquid drug from a first reservoir may be pumped from the first reservoir into the patient at a first time, before liquid drug from a second reservoir may be pumped from the second reservoir into the patient at a later second time.

The treatment fluid need not be insulin but could be any of a number of liquid drugs. Multiple forms of medication or mixtures of medication can be stored in separate removable modules for later mixing in a co-formulated dosing or connected to separate pump elements on the wearable device. Drugs stored in the device may include, but are not limited to, insulin, hyaluronidase, analgesics, or others.

In some examples, a drug reservoir may connect with an external detector.

Sensor Modules

In some examples, the device may include one or more sensor module. Some sensors are discussed herein, but other sensors may be included in the wearable device. In some examples, a sensor module may connect to an external detector which may noninvasively, minimally invasively, or invasively secure to the patient. In some examples, a single detector may connect with more than one sensor module. It may be advantageous to pair a sensor with a drug administration module. For example, there may be an advantage to pair a sensor which measures glucose concentration in the patient's blood with an insulin administration module such that the patient may receive an appropriate amount of insulin relative to the blood concentration of glucose.

Sensor modules may be removed from the modular wearable device for reuse.

Analyte Sensors

In some examples, the modular wearable device may include a removable module having an analyte sensor. An analyte sensor may, for instance, connect to an external detector that may be noninvasively, minimally invasively, or invasively secured to the patient. In some examples, an analyte sensor may be a glucose sensor, a lipid sensor, a lactic acid sensor, a ketone sensor, an oxygen sensor, or a carbon dioxide sensor. However, an analyte sensor may measure presence or concentration of any other analyte of interest.

Microphones

In some examples, the modular wearable device may include a sensor module having a microphone. A microphone module may be disposable or replaceable. A microphone may enable detection of a variety of physiological parameters, including: respiration, joint movement, muscle contraction, burping, hiccups, spasms, swallowing, stomach churn, pylorus noises, small intestine noises, and/or large intestine noises. A microphone module may measure any physiological parameter which may be sensed acoustically.

Optical Sensors

In some examples, the modular wearable device may include a sensor module which includes an optical sensor. Optical sensor modules may be connected by polymer base fibers or glass fibers. Glass fibers of any type may run through reinforced channeling, similar to the fluid channels discussed above, but with reduced maximum flexion. Distribution of optical systems, including fiber optic connections and the sensor modules themselves, across the device may enable less obtrusive wear.

Tissue Coupling

In some examples, the modular device may include a sensing module including miniaturized optical lenses or fibers. The miniaturized optical lenses or fibers may be used to deliver excitation light into skin or tissue and to collect Raman or fluorescence light emitting from skin or tissue.

Excitation Beam Sensors

In some examples, the modular device may include a sensing module that can emit an excitation beam. For example, a wavelength stabilized laser diode may be used as an excitation light source. The light source may be coupled to optical fibers to delivered the excitation beam to the tissue coupling compartment.

Optical Coherence Tomography Sensors

In some examples, the modular device may include a sensing module capable of time domain or spectral domain optical coherence tomography (OCT). OCT may be used to characterize skin and/or tissue depth information. Advantageously, the characterization of skin and/or tissue depth information may help facilitate signal processing. In some examples, optical fibers may be used to connect a tissue coupling module and an OCT module. In some examples, tissue coupling technology and OCT technology may be integrated within a single removable module.

Spectrophotometer Sensors

In some examples, the modular device may include a sensing module that can make spectrophotometric measurements. For example, a spectrophotometer module may measure diffraction, interference, and/or absorption. A spectrophotometer may be miniaturized to fit within a removable module having a sufficiently low profile to enable unobtrusive wear. A spectrophotometer module may have a photosensor, for example a CMOS, CCD, or photodiode.

The photo-sensor of the spectrophotometer may be electronically connected with a SOC. In some examples, a spectrophotometer module may be connected, for example by optical fibers, with a tissue coupling module. In some examples, a spectrophotometer and a tissue coupling apparatus may be integrated within a single removable module. In some examples, a single module may integrate OCT technology and spectrophotometer technology. In some examples, a spectroscopic module may be reused. For example, the spectroscopic module may be removed from the modular device to be re-attached to a different modular device.

Movement Sensors

In some examples, the modular device may include a sensing module that can sense motion and/or position of the wearer. For example, movement sensors may include linear and angular accelerometers, inertial sensors, and/or a GPS sensor.

Other Example Modules

The modular device may include removable modules that are neither drug delivery reservoir modules nor sensor modules.

Batteries

In some examples, the modular wearable device may include batteries. In some examples, batteries may be incorporated into removable modules including another apparatus. For instance, a drug pump and a battery may be integrated into the same removable module. In some examples, a removable module may include one or more batteries but no other apparatuses. Arrays of small batteries in series or parallel may be included within a removable module to enable unobtrusive battery upgrades to systems of various size. In some examples, a removable module may include a replaceable battery pack. Advantageously, if the charge of a removable module having one or more battery is low, a user may easily swap it for a removable module having one or more charged batteries.

Wireless Modules

In some examples, wireless modules may also be included as a removable module in the modular wearable device. A wireless module may serve as a personal connectivity hub. A wireless module may include a Bluetooth transceiver, a wifi transceiver, a wireless broadband transceiver (for example, a transceiver that may send or receive signals of type: 2g, 3g, 4g, LTE, 5g, etc.), a near field communication (NFC) transceiver, an optical transceiver, an acoustic transceiver, or other apparatus for conveying and/or receiving information wirelessly.

Charging Points for Various Modules

In some examples, the modular wearable device may include one or more charging points for removable modules. A charging point may charge any modular item that can be exchanged into module receiving portions of the wearable device. A charging point may be connected to, for example, a module having one or more batteries.

Example Devices

Figure 7A:
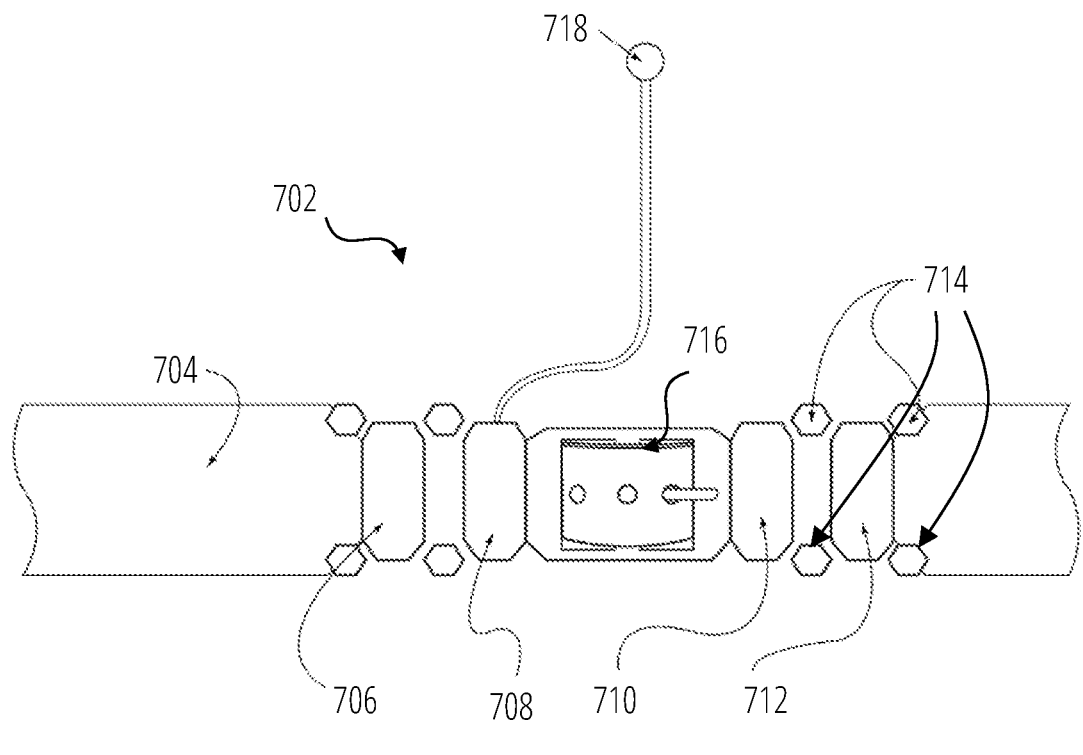
FIG. 7A illustrates a first example modular wearable device from a front view.
Figure 7B:
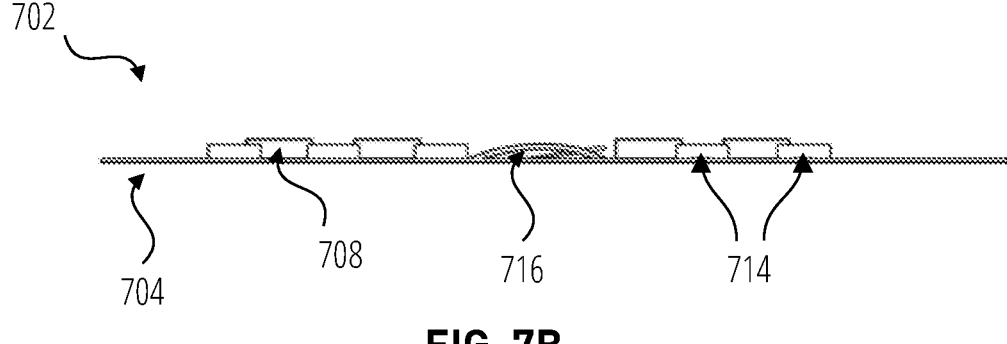
FIG. 7B illustrates the modular wearable device of FIG. 7A from a side view.

In one example, diagrammed in FIG. 7A in an overhead view and in FIG. 7B in a top view, the modular wearable device 702 may include a flexible material 704, a removable module 706, a removable module 708, a removable module 710, a removable module 712, batteries 714, a fastening portion 716, and an external detector 718. The removable modules 706, 708, 710, and 712 may sit within module receiving portions. Removable modules 706, 708, 710, and 712 can be removed from the modular wearable device.

The removable modules 706, 708, 710, and 712 may include drug delivery reservoirs, physiological sensors, or wireless modules. The removable module 708 may, for example, include a physiological sensor connected to external detector 718. The fastening portion 716 may be any of several mechanisms, for example: an elastic strap, a belt buckle, a hook and loop, a tie, a hook and loop fastener, a zipper, a hole and button, a toggle, a snap fastener, a grommet, a magnet, or a cord lock. In the example of FIG. 7A and FIG. 7B, fastening portion 716 is diagrammed as a belt buckle. Fastening portion 716 may be used to removably affix the modular wearable device 802 to a patient or to adjust the fit of the modular wearable device 702 on the patient.

Figure 8A:
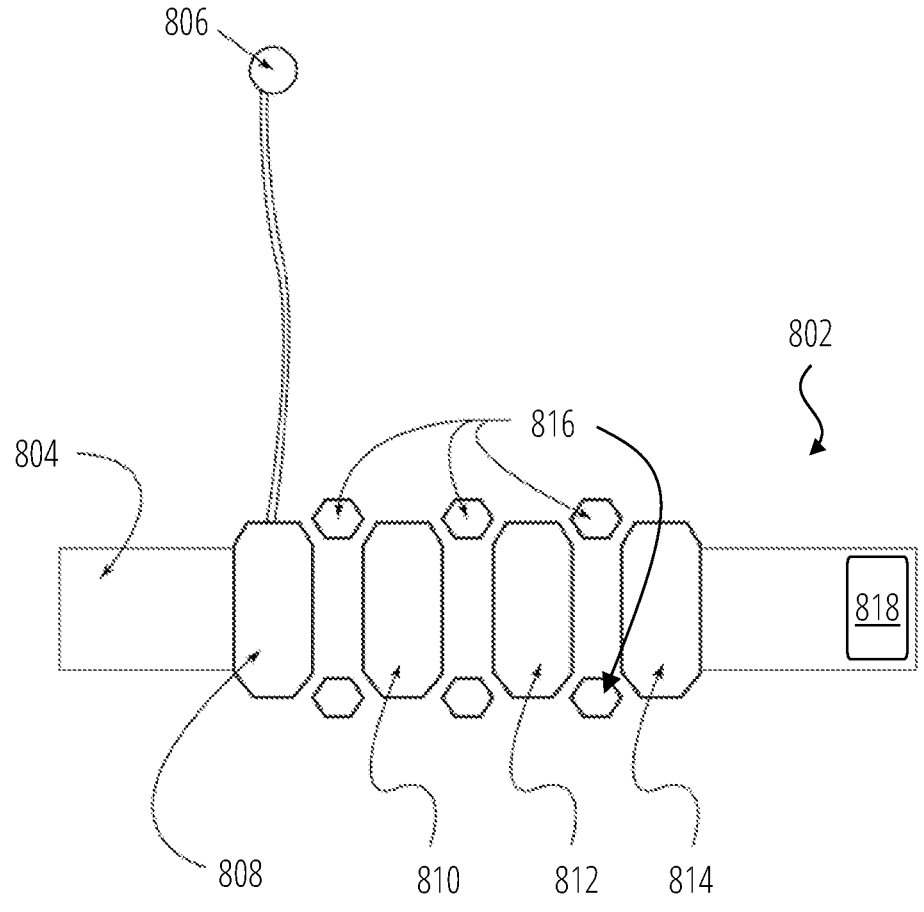
FIG. 8A illustrates a second example modular wearable device from a front view.
Figure 8B:
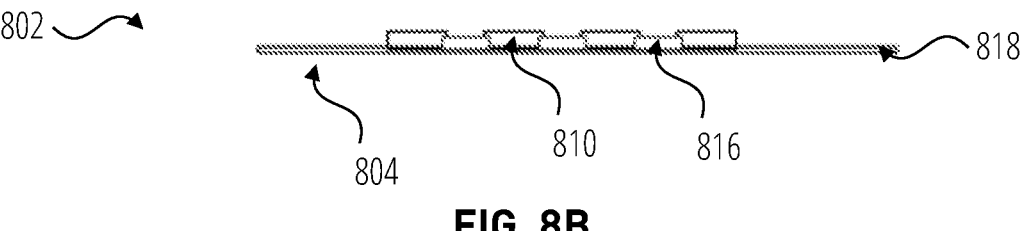
FIG. 8B illustrates the modular wearable device of FIG. 8A from a side view.

In another example, diagrammed in FIG. 8A in an overhead view and in FIG. 8B in a top view, the modular wearable device 802 includes a flexible material 804, an external detector 806, a removable module 808, a removable module 810, a removable module 812, a removable module 814, batteries 816, and a fastening portion 818. The removable modules 808, 810, 812, and 814 may sit within module receiving portions. The removable modules 808, 810, 812, and 814 may be removed from the modular wearable device.

The removable modules 808, 810, 812, and 814 may further include drug delivery reservoirs, physiological sensors, or wireless modules. The removable module 808 may, for example, further include a physiological sensor connected to an external detector 806. The fastening portion 818 may be any of several mechanisms, for example: an elastic strap, a belt buckle, a hook and loop, a tie, a hook and loop fastener, a zipper, a hole and button, a toggle, a snap fastener, a grommet, a magnet, or a cord lock. In the example of FIG. 8A and FIG. 8B, fastening portion 818 is diagrammed as a hook and loop fastener. The fastening portion 818 may be used to removably affix the modular wearable device 802 to a patient or to adjust the fit of the modular wearable device 802 on the patient.

Figure 9:
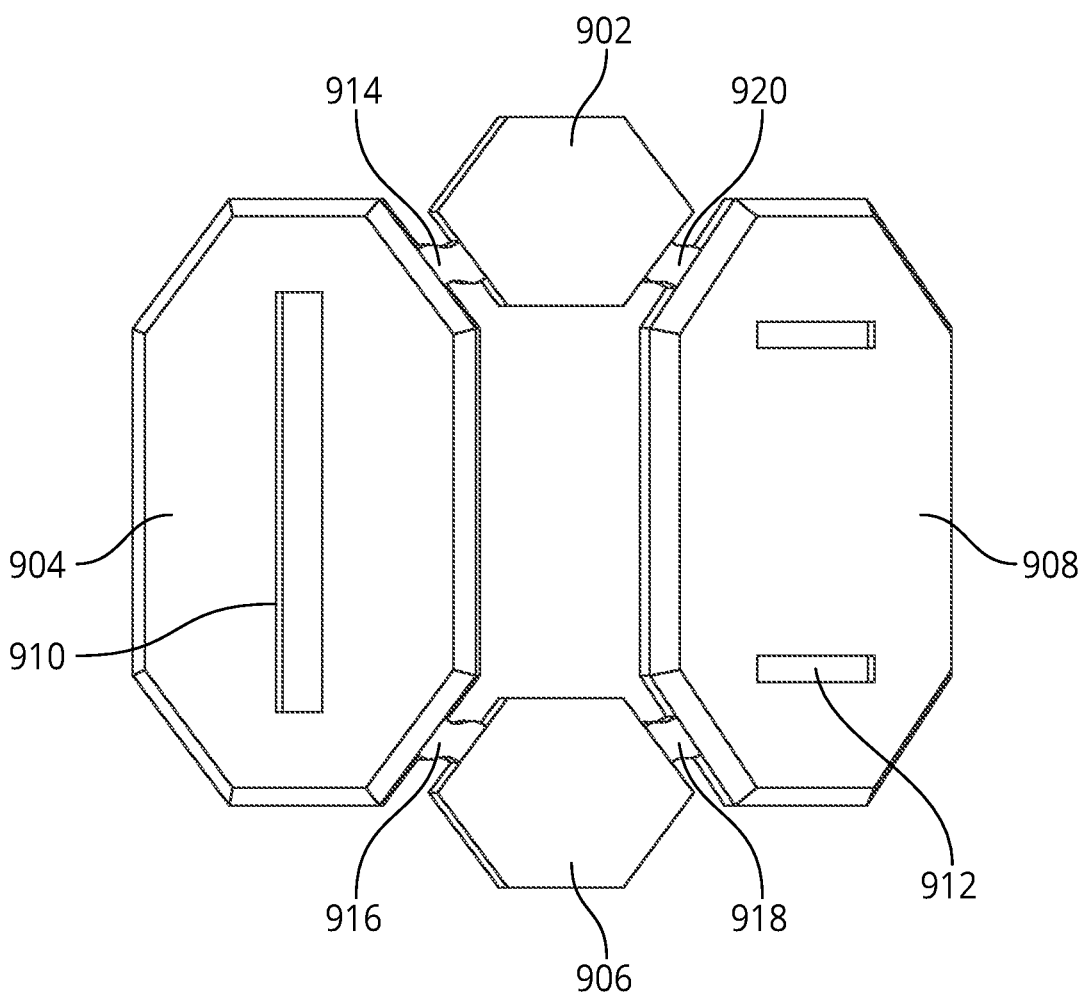
FIG. 9 illustrates an example grouping or arrangement of removable modules and the example connections between the removable modules.

In one example, a removable module may connect with one or more other removable modules. FIG. 9 illustrates a set of four removable modules including a physiological sensor 902, a drug delivery reservoir 904, a battery module 906, and a removable module 908. The physiological sensor 902 may connect with the drug delivery reservoir 904 via a signaling connection 914. The physiological sensor 902 may connect with the battery module 906 via power connection 916. The removable module 908 may connect to physiological sensor 902 via a signaling connection 920. The removable module 908 may connect to a battery module 906 via power connection 918. The drug delivery reservoir 904 may contain liquid drug and include a window 910 through which the remaining level of liquid drug may be visible.

The removable module 908 may, for example, include a printed circuit board. The removable module 908 may also include a status indicator 912. The status indicator 912 may, for example, indicate a status of one or more modules, the wearable modular device, a disease state or state of the patient, the like or a combination thereof. For example, the status indicator 912 may indicate that charge of the battery module 906 is low. The status indicator may exhibit a pattern of light to alert a user or patient to the status of the module. For example, a status indicator may exhibit a low battery status by flashing a red light. Status indicator 912 may be used to convey other information by other means, including but not limited to, an audible alert, color of status light, digital display, tactile or vibratory alert, the like or a combination thereof.

Figure 10:
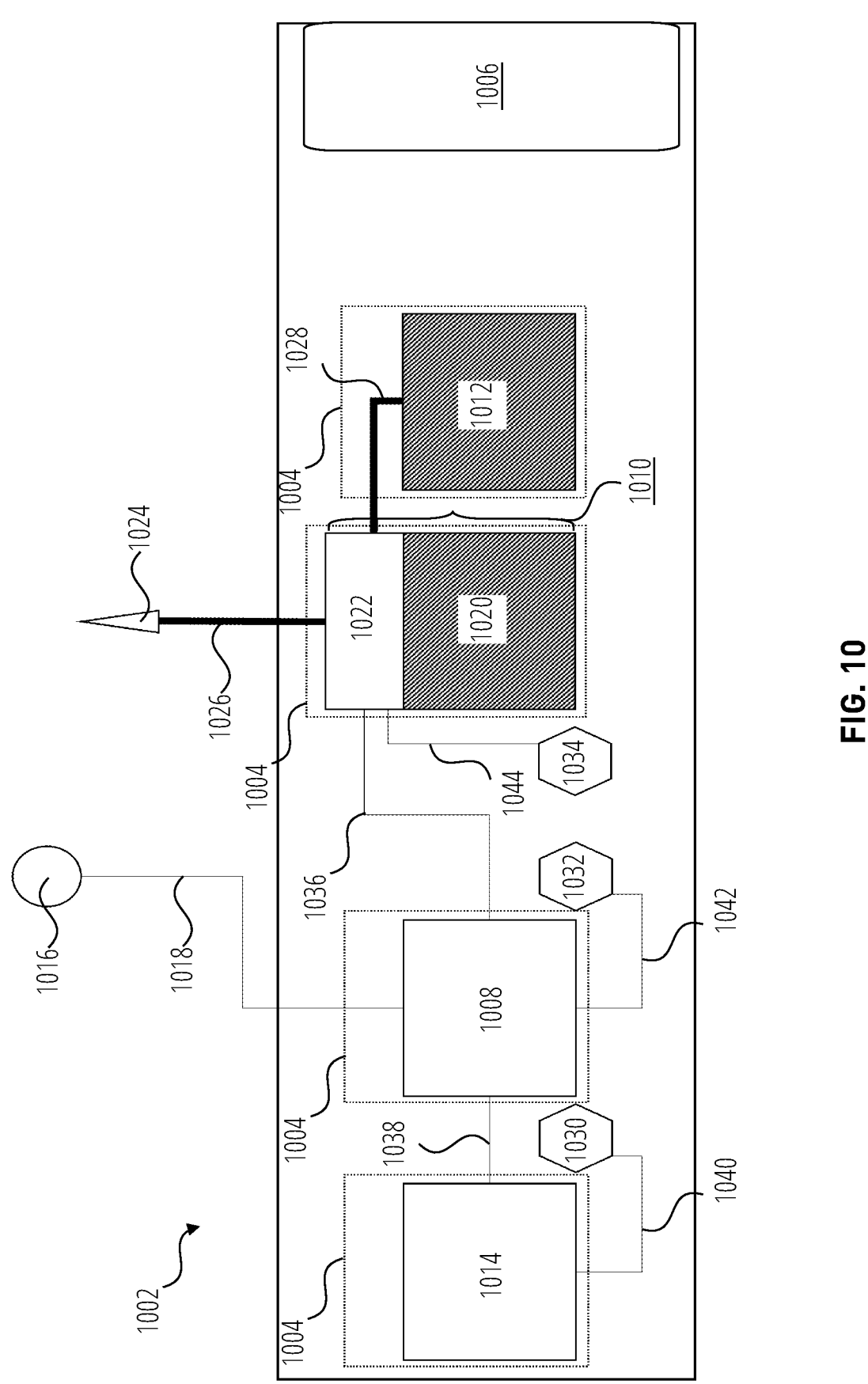
FIG. 10 schematically illustrates an example of the modular wearable device in which various removable modules may be interconnected.

In one example, the modular wearable device may include several removable modules that can communicate with other removable modules and/or components of the modular wearable device and/or connections between modules. FIG. 10 schematically illustrates an example wherein the modular wearable device 1002 includes several module receiving portions 1004. The modular wearable device 1002 includes a fastening portion 1006, and removable modules 1008, 1014, 1010 and 1012. Removable module 1008 includes a physiological sensor in communication with an external detector 1016 via signaling connection 1018.

Removable module 1010 includes a drug delivery reservoir. The drug delivery reservoir 1010 includes a liquid drug compartment 1020 fluidically connected to a drug pump 1022. The drug pump 1022 connects to a cannula 1024 via a fluid channel 1026 to inject liquid drug to the patient. Removable module 1012 may include a second drug delivery reservoir including a liquid drug compartment. The drug delivery reservoir 1012 connects to the drug pump 1022 via a fluid channel 1028. The drug pump 1022 may mix the liquid drugs pumped from liquid drug compartment 1020 and drug delivery reservoir 1012. Either drug delivery reservoir may include insulin, hyaluronidase, or an analgesic.

The removable module 1014 may be a wireless module. The wireless module 1014 may further include an optical transceiver, an acoustic transceiver, a Bluetooth transceiver, a GPS transceiver, a Wi-Fi transceiver, or a wireless broadband transceiver.

The modular wearable device may also include a battery 1030, a battery 1032, a battery 1034. The battery 1030 can connect to wireless module 1014 via power connection 1040, while the battery 1032 connects to the physiological sensor 1008 via a power connection 1042, and the battery 1034 connects to the drug pump 1022 via a power connection 1044. The physiological sensor 1008 connects to the drug pump 1022 via a signaling connection 1036. The physiological sensor 1008 connects to the wireless module 1014 via a signaling connection 1038.

As depicted in FIG. 10, the external detector 1016 can connect to removable physiological sensor 1008 via signaling connection 1018. As diagrammed, the signaling connection 1018 may be a wired connection. However, the signaling connection 1018 may alternatively be a wireless connection between the physiological sensor 1008 and the external detector 1016. External detectors may be connected to sensor modules or drug delivery reservoirs via wired and/or wireless connections.

Figure 11:
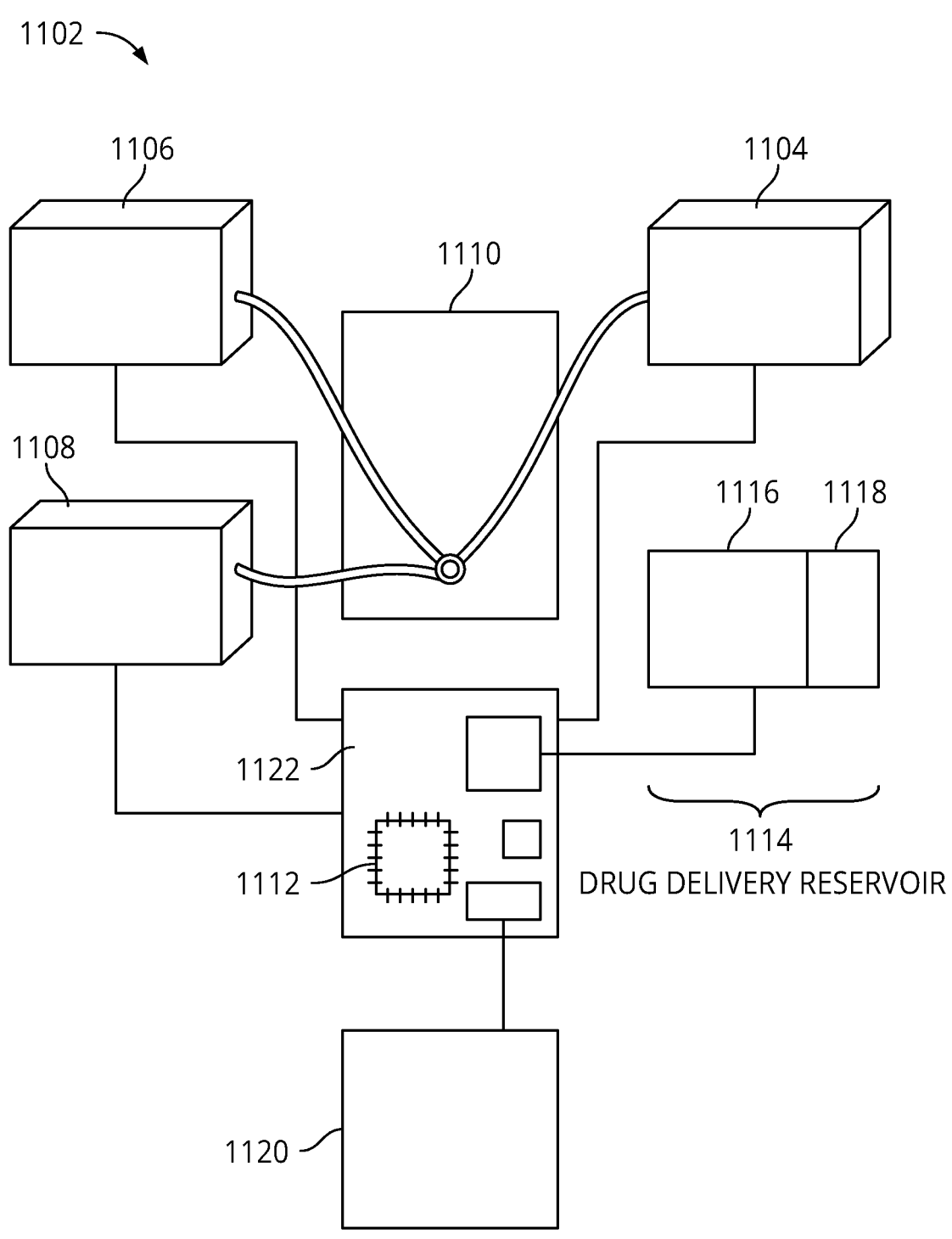
FIG. 11 illustrates example components of the modular wearable device.

In one example, the modular wearable device may include several removable modules and connections between modules. FIG. 11 schematically illustrates an example wherein the modular wearable device 1102 includes several modules and module components, including a Raman sensor 1104, an OCT sensor 1106, a light emitter 1108, an external detector 1110, a SoC 1112, a drug delivery reservoir 1114, a drug pump 1116, a liquid drug compartment 1118, a battery module 1120, and a printed circuit board 1222.

The drug delivery reservoir 1114 may be a single removable module which integrates a drug pump 1116 and a liquid drug compartment 1118 housing insulin. The liquid drug compartment 1118 may be of any volume that can be carried by the modular wearable device 1102. The liquid drug compartment 1118 may have a volume of, for example, 3.75 mL.

The OCT sensor 1106, the light emitter 1108, and the Raman sensor 1104 may be connected with the external detector 1110 via a signaling connection such that information may be communicated. The OCT sensor 1106, the light emitter 1108, and the Raman sensor 1104 may be connected to printed circuit board 1122, which may be used to integrate information received. The printed circuit board 1122 may include a SoC 1112 which may process incoming signals and output signals. For example, the SoC 1112 might output information to the drug pump 1116 to specify a pump rate ensuring insulin administration at a target rate. The printed circuit board 1122 may be connected to the battery module 1120 such that the battery module 1120 provides electricity to power the printed circuit board 1122. The battery module 1120 may include more than one battery. For example, FIG. 11 represents the battery module 1120 as including five batteries. The printed circuit board 1122 may provide electrical power to the other modules on the belt via the aforementioned connections.

Terminology

Unless defined otherwise, all technical and scientific terms used herein have the same meaning as is commonly understood by one of ordinary skill in the art. The use of the term "including" as well as other forms, such as "include," "includes," and "included," is not limiting. The use of the term "having" as well as other forms, such as "have," "has," and "had," is not limiting. The terms "comprising," "including," "having," and the like are synonymous and are used inclusively, in an open-ended fashion, and do not exclude additional elements, features, acts, operations, and so forth. That is, the above terms are to be interpreted synonymously with the phrases "having at least" or "including at least." For example, when used in the context of a process, the term "comprising" means that the process includes at least the recited steps, but may include additional steps. When used in the context of a device, the term "comprising" means that the device includes at least the recited features or components, but may also include additional features or components. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain implementations, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The term "and/or" as used herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

Conditional language used herein, such as, among others, "can," "could," "might," "may," "e.g.," and the like, unless specifically stated otherwise, or otherwise understood within the context as used, is generally intended to convey that certain, certain features, elements and/or steps are optional. Thus, such conditional language is not generally intended to imply that features, elements and/or steps are in any way required or that one or more implementations necessarily include logic for deciding, with or without other input or prompting, whether these features, elements and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Any methods disclosed herein need not be performed in the order recited. The methods disclosed herein include certain actions taken by a practitioner; however, they can also include any third-party instruction of those actions, either expressly or by implication.

The methods and tasks described herein may be performed and fully automated by a computer system. The computer system may, in some cases, include multiple distinct computers or computing devices (for example, physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (for example, solid state storage devices, disk drives, etc.). The various functions disclosed herein may be embodied in such program instructions, and/or may be implemented in application-specific circuitry (for example, ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. The computer system may be a cloud-based computing system whose processing resources are shared by multiple distinct business entities or other users.

While the above detailed description has shown, described, and pointed out novel features, it can be understood that various omissions, substitutions, and changes in the form and details of the devices or algorithms illustrated can be made without departing from the spirit of the disclosure. As can be recognized, certain portions of the description herein can be embodied within a form that does not provide all of the features and benefits set forth herein, as some features can be used or practiced separately from others. The scope of certain implementations disclosed herein is indicated by the appended claims rather than by the foregoing description. All changes which come within the meaning and range of equivalency of the claims are to be embraced within their scope.

What is claimed is:

1. A modular wearable device for patient monitoring and drug delivery, the modular wearable device comprising:
   a fastening portion configured to removably affix the modular wearable device to a portion of a patient;
   a plurality of module receiving portions configured to receive removable modules;
   a first removable module comprising a physiological sensor; and
   a second removable module comprising a first drug delivery reservoir and a pump in fluid connection with a cannula and the first drug delivery reservoir, the pump configured to deliver liquid drug from the first drug delivery reservoir to the patient, wherein the first drug delivery reservoir is configured to deform as liquid drug is dispensed,
   wherein the first module and the second module are in communication.

2. The modular wearable device of claim 1, wherein the modular wearable device is configured to removably affix to at least one of: the patient's arm, the patient's leg, the patient's waist, or the patient's chest.

3. The modular wearable device of claim 1, wherein the module receiving portions are configured to accept, hold, and release the removable modules.

4. The modular wearable device of claim 1, further comprising a third removable module comprising a battery, the modular wearable device comprising a power connection between the battery and at least one other removable module.

5. The modular wearable device of claim 1, comprising a third removable module comprising a wireless module.

6. The modular wearable device of claim 5, wherein the wireless module comprises at least one of: an optical transceiver, an acoustic transceiver, a Bluetooth transceiver, a GPS transceiver, a Wi-Fi transceiver, or a wireless broadband transceiver.

7. The modular wearable device of claim 1, wherein the physiological sensor comprises an external detector configured to removably affix to the patient.

8. The modular wearable device of claim 1, wherein the physiological sensor comprises at least one of: an analyte sensor, an inertial measurement sensor, a skin impedance sensor, a microphone, a haptic sensor, an optical sensor, a pulse measurement sensor, a diffuse reflectance sensor, or a Raman sensor.

9. The modular wearable device of claim 8, wherein the analyte sensor comprises at least one of: a glucose sensor, a lipid sensor, a lactic acid sensor, a ketone sensor, an oxygen sensor, or a carbon dioxide sensor.

10. The modular wearable device of claim 1, wherein the drug delivery reservoir comprises insulin, hyaluronidase, or an analgesic.

11. The modular wearable device of claim 1, wherein the modular wearable device comprises a fluid channel configured to inject a liquid drug into the patient.

12. The modular wearable device of claim 11, wherein the fluid channel is configured to resist deformation.

13. The modular wearable device of claim 11, wherein the modular wearable device comprises a second fluid channel connecting the first drug delivery reservoir to a second drug delivery reservoir.

14. The modular wearable device of claim 13, wherein the second fluid channel is configured to mix liquid drug from the first drug delivery reservoir and second drug delivery reservoir.

15. The modular wearable device of claim 13, wherein the second fluid channel is configured to resist deformation.

16. The modular wearable device of claim 1, wherein the modular wearable device comprises a signaling connection between the physiological sensor and at least one other module.

17. The modular wearable device of claim 1, wherein the modular wearable device comprises a flexible material that is configured to conform to an attachment site on the patient.

* * * * *